United States Patent
Gelfman et al.

(10) Patent No.: US 12,157,891 B2
(45) Date of Patent: Dec. 3, 2024

(54) TREATMENT OF UVEITIS WITH ENDOPLASMIC RETICULUM AMINOPEPTIDASE 1 (ERAP1) INHIBITORS

(71) Applicant: Regeneron Pharmaceuticals, Inc., Tarrytown, NY (US)

(72) Inventors: Sahar Gelfman, Tarrytown, NY (US); Ann Ligocki, Tarrytown, NY (US); Giovanni Coppola, Tarrytown, NY (US); Aris Baras, Tarrytown, NY (US); Arden Moscati, Tarrytown, NY (US); Eli A. Stahl, Tarrytown, NY (US); Carmelo Romano, Tarrytown, NY (US); Santiago Mendez Huergo, Tarrytown, NY (US); Jonathan Weyne, Tarrytown, NY (US); Tave Van Zyl, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/046,291

(22) Filed: Oct. 13, 2022

(65) Prior Publication Data
US 2023/0250434 A1    Aug. 10, 2023

Related U.S. Application Data

(60) Provisional application No. 63/328,008, filed on Apr. 6, 2022, provisional application No. 63/255,597, filed on Oct. 14, 2021.

(51) Int. Cl.
| | |
|---|---|
| *C12N 15/113* | (2010.01) |
| *A61P 27/02* | (2006.01) |
| *C12N 9/22* | (2006.01) |
| *C12Q 1/37* | (2006.01) |

(52) U.S. Cl.
CPC .......... *C12N 15/1137* (2013.01); *A61P 27/02* (2018.01); *C12N 9/22* (2013.01); *C12Q 1/37* (2013.01); *C12N 2310/11* (2013.01); *C12N 2310/14* (2013.01); *G01N 2333/96425* (2013.01)

(58) Field of Classification Search
CPC .......... C12N 15/113; C12N 2310/141; C12N 2310/315; C12N 2310/321; C12N 2310/323; C12N 2310/3341; C12N 2310/346; C12N 2310/14; A61P 25/28; C07K 16/18
See application file for complete search history.

(56) References Cited

U.S. PATENT DOCUMENTS

| | | | | |
|---|---|---|---|---|
| 8,968,731 B2 * | 3/2015 | Wicks | ..................... | A61P 27/02 424/143.1 |
| 2013/0259876 A1 * | 10/2013 | Murphy | .................. | A61P 37/00 424/173.1 |
| 2013/0315933 A1 * | 11/2013 | Renner | .............. | C07K 16/2833 435/69.6 |

FOREIGN PATENT DOCUMENTS

| | | | | |
|---|---|---|---|---|
| WO | 2012047294 | 4/2012 | | |
| WO | WO-2014155278 A2 * | 10/2014 | .......... | C07K 16/244 |
| WO | 2021094763 | 5/2021 | | |
| WO | 2022026336 | 2/2022 | | |

OTHER PUBLICATIONS

Huang et al. "Genomewide Association Study of Acute Anterior Uveitis Identifies New Susceptibility Loci", Jun. 2020, IOVS, vol. 61 pp. 1-10. (Year: 2020).*
preventblindness.org [retrieved on Nov. 17, 2023]. Retrieved from the Internet: <URL: https://preventblindness.org/how-do-eye-doctors-treat-uveitis/> (Year: 2023).*
Plenge et al. "Validating therapeutic targets through human genetics", Published Jul. 2013, Nature Reviews Drug Discovery, vol. 12, p. 586. (Year: 2013).*
Kuiper et al., "Functionally distinct ERAP1 and ERAP2 are a hallmark of HLA-A29-(Birdshot) Uveitis", Human Molecular Genetics, 2018, 27(24), pp. 4333-4343.
Dimopoulou et al., "Variant in ERAP1 promoter region is associated with low expression in a patient with a Behcet-like MHC-I-opathy", Journal of Human Genetics, 2019, 65(3), pp. 325-335.
Doench et al., "Optimized sgRNA design to maximize activity and minimize off-target effects of CRISPR-Cas9", Nature Biotechnology, 2016, 34(2), pp. 184-191.
Akkoc et al., "Ankylosing Spondylitis: HLA-B*27-Positive Versus HLA-B*27-Negative Disease", Current Rheumatology Reports, 2017, 19(5), pp. 1-11.
Takeuchi et al., "Pathogenesis of Non-Infectious Uveitis Elucidated by Recent Genetic Findings", Frontiers in Immunology, 2021, 12, pp. 1-14.
Huang et al., "Genomewide Association Study of Acute Anterior Uveitis Indentifies New Susceptibility Loci", Investigative Opthalmology & Visual Science, 2020, 61(6), pp. 3-12.
Robinson et al., "The genetic association of acute anterior uveitis and their overlap with the genetics of ankylosing spondylitis", Genes and Immunity, 2016, 17(1), pp. 46-51.
Nossent et al., "The influence of ERAP1 gene variants on clinical phenotype in ankylosing spondylitis", Scandinavian Journal of Rheumatology, 2016, 45(6), pp. 474-479.

(Continued)

*Primary Examiner* — Brian Whiteman
*Assistant Examiner* — Stephanie L Sullivan
(74) *Attorney, Agent, or Firm* — Armstrong Teasdale LLP

(57) ABSTRACT

The present disclosure provides methods of treating subjects having uveitis, and methods of identifying subjects having an increased risk of developing uveitis.

9 Claims, 4 Drawing Sheets

Specification includes a Sequence Listing.

(56) References Cited

OTHER PUBLICATIONS

Robinson et al., "Genetic Dissection of Acute Anterior Uveitis Reveals Similarities and Differences in Associations Observed With Ankylosing Spondylitis: Genetics of Anterior Uveitits", Arthritis & Rheumatology, 2015, 67(1), pp. 140-151.

Kuiper et al., "HLA-A29 and Birdshot Uveitis: Further Down the Rabbit Hole", Frontiers in Immunology, 2020, 11, pp. 1-14.

\* cited by examiner

TREATMENT OF UVEITIS WITH ENDOPLASMIC RETICULUM AMINOPEPTIDASE 1 (ERAP1) INHIBITORS

REFERENCE TO SEQUENCE LISTING

This application includes a Sequence Listing submitted electronically as an XML file named 381203619SEQ, created on Oct. 11, 2022, with a size of 4,806 kilobytes. The Sequence Listing is incorporated herein by reference.

FIELD

The present disclosure relates generally to the treatment of subjects having uveitis, such as anterior uveitis, with Endoplasmic Reticulum Aminopeptidase 1 (ERAP1) inhibitors, and methods of identifying subjects having an increased risk of developing uveitis.

BACKGROUND

Anterior uveitis (AU) is an inflammation of the middle layer of the eye. This middle layer includes the iris (colored part of the eye) and adjacent tissue, known as the ciliary body. Anterior uveitis can result from a trauma to the eye, such as being hit in the eye or having a foreign body in the eye. It can also be associated with general health problems such as rheumatoid arthritis, syphilis, tuberculosis, sarcoid, viral (herpes simplex, herpes zoster, cytomegalovirus) or idiopathic, which is no obvious underlying cause. Acute anterior uveitis (AAU) involves inflammation of the iris and ciliary body of the eye. AAU occurs both in isolation and as an extra-articular feature of ankylosing spondylitis (AS). It is potentially sight threatening and can cause ophthalmological sequelae such as cataracts, posterior synechiae, and glaucoma. Uveitis accounts for about 10% of those individuals with severe vision impairment and blindness. The prevalence of anterior uveitis is approximately 0.1-0.3% (1-3:1,000). About 300,000-350,000 cases of uveitis occur in the United States. AAU occurs in 30-40% of individuals with AS and increases in frequency with disease duration such that the prevalence in individuals with AS for >50 years approaches 60%. AAU is known to be associated with HLA-B*27 independently of the association of this allele with AS (~50% of affected individuals are HLA-B*27 carriers).

Endoplasmic Reticulum Aminopeptidase 1 (ERAP1) is an aminopeptidase involved in trimming of HLA class I-binding precursors, a step required for the generation of most HLA class I-binding peptides so that they can be presented on MHC class I molecules. Peptide trimming is essential to customize longer precursor peptides to fit them to the correct length required for presentation on MHC class I molecules. ERAP1 acts as a monomer or as a heterodimer with ERAP2. ERAP1 strongly prefers substrates 9-16 residues long, rapidly degrades 13-mer to a 9-mer and then stops. ERAP1 preferentially hydrolyzes the residue Leu and peptides with a hydrophobic C-terminus, while it has weak activity toward peptides with charged C-terminus.

SUMMARY

The present disclosure provides methods of treating a subject having uveitis, the methods comprising administering an ERAP1 inhibitor to the subject.

The present disclosure also provides methods of treating a subject having iridocyclitis, the methods comprising administering an ERAP1 inhibitor to the subject.

The present disclosure also provides methods of treating a subject having iritis, the methods comprising administering an ERAP1 inhibitor to the subject.

The present disclosure also provides methods of treating a subject with a therapeutic agent that treats or inhibits uveitis, wherein the subject has uveitis, the methods comprising: determining whether the subject has an ERAP1 variant nucleic acid molecule by: obtaining or having obtained a biological sample from the subject; and performing or having performed a sequence analysis on the biological sample to determine if the subject has a genotype comprising the ERAP1 variant nucleic acid molecule; and administering or continuing to administer the therapeutic agent that treats or inhibits uveitis in a standard dosage amount to a subject that is ERAP1 reference, and/or administering an ERAP1 inhibitor to the subject; and administering or continuing to administer the therapeutic agent that treats or inhibits uveitis in an amount that is the same as or less than a standard dosage amount to a subject that is heterozygous for the ERAP1 variant nucleic acid molecule, and/or administering an ERAP1 inhibitor to the subject; wherein the presence of a genotype having the ERAP1 variant nucleic acid molecule indicates the subject has a decreased risk of developing uveitis.

The present disclosure also provides methods of identifying a subject having an increased risk of developing uveitis, the methods comprising: determining or having determined the presence or absence of an ERAP1 variant nucleic acid molecule in a biological sample obtained from the subject; wherein: when the subject is ERAP1 reference, then the subject has an increased risk of developing uveitis; and when the subject is heterozygous or homozygous for an ERAP1 variant nucleic acid molecule, then the subject has a decreased risk of developing uveitis.

The present disclosure also provides therapeutic agents that treat or inhibit uveitis for use in the treatment of uveitis in a subject identified as having: i) an ERAP1 variant genomic nucleic acid molecule, or the complement thereof, wherein the genomic nucleic acid molecule has a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; ii) an ERAP1 variant mRNA molecule, or the complement thereof, wherein the mRNA molecule has a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof; or iii) an ERAP1 variant cDNA molecule, or the complement thereof, wherein the cDNA molecule has a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

The present disclosure also provides ERAP1 inhibitors for use in the treatment of uveitis in a subject that: a) is reference for an ERAP1 genomic nucleic acid molecule, an ERAP1 mRNA molecule, or an ERAP1 cDNA molecule; or b) is heterozygous for: i) an ERAP1 variant genomic nucleic acid molecule, or the complement thereof, wherein the genomic nucleic acid molecule has a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; ii) an ERAP1 variant mRNA molecule, or the complement thereof, wherein the mRNA molecule has a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof; or iii) an ERAP1 variant cDNA molecule, or the complement thereof, wherein the cDNA molecule has a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

BRIEF DESCRIPTION OF THE DRAWINGS

The accompanying figures, which are incorporated in and constitute a part of this specification, illustrate several features of the present disclosure.

DESCRIPTION

Figure 1:
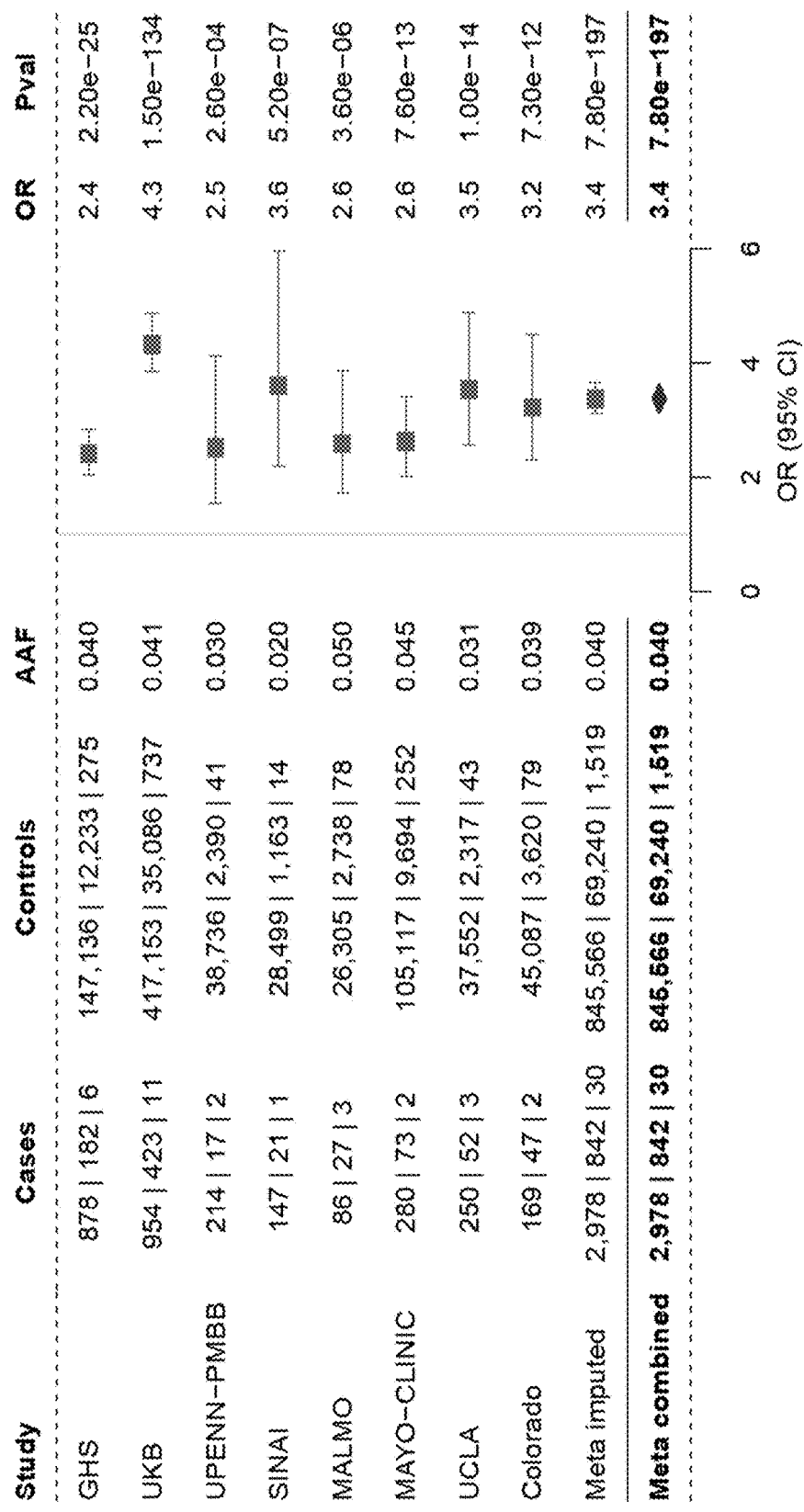
FIG. 1 shows Forest plots of the top single nucleotide polymorphisms (SNPs) in the HLA-B27 (Panel A) and ERAP1 (Panel B) loci.
Figure 1:
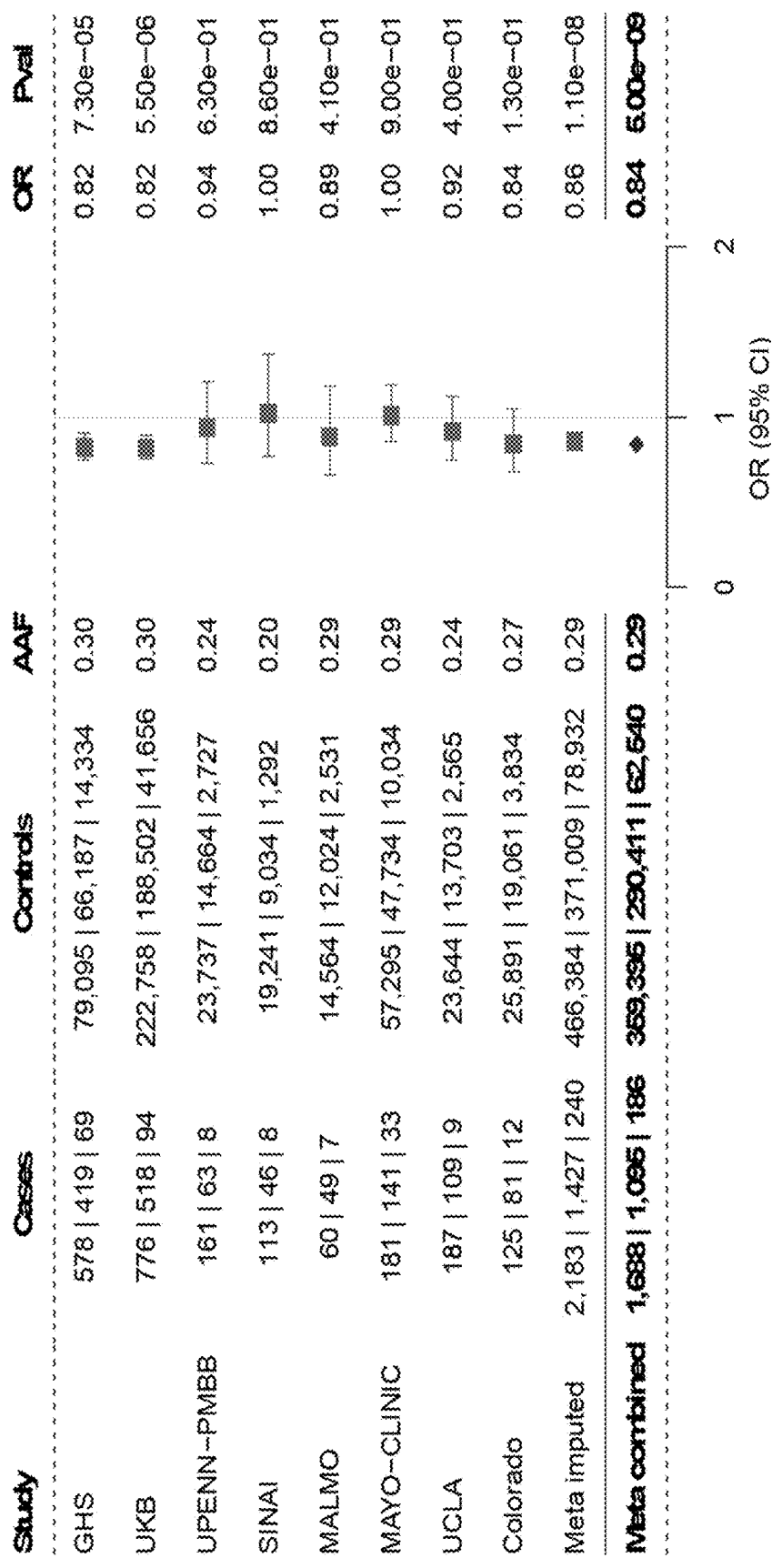

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is not intended that any method or aspect set forth herein be construed as requiring that its steps be performed in a specific order. Accordingly, where a method claim does not specifically state in the claims or descriptions that the steps are to be limited to a specific order, it is not intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or other tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

Variants in the ERAP1 gene that result in reduced expression of ERAP1 or that result in an ERAP1 predicted loss-of-function polypeptide associated with a decreased risk of developing uveitis, such as anterior uveitis, acute anterior uveitis, iridocyclitis, iritis, and pan-uveitis, in humans has been identified in accordance with the present disclosure. For example, a genetic alteration that changes the adenine at position 19,474 in the ERAP1 reference genomic nucleic acid molecule (see, SEQ ID NO:1) to a guanine, or changes the guanine at position 21,595 in the ERAP1 reference genomic nucleic acid molecule (see, SEQ ID NO:1) to an adenine, or changes the thymine at position 21,811 in the ERAP1 reference genomic nucleic acid molecule (see, SEQ ID NO:1) to a cytosine, or changes the cytosine at position 42,579 in the ERAP1 reference genomic nucleic acid molecule (see, SEQ ID NO:1) to a thymine has been observed to indicate that the subject having such an alteration may have a decreased risk of developing uveitis. Altogether, the genetic analyses described herein surprisingly indicate that the ERAP1 gene and, in particular, a variant in the ERAP1 gene, associates with a decreased risk of developing uveitis. In some embodiments, this association is independent of HLA-B*27. In some embodiments, this association is synergistic with HLA-B*27. Therefore, subjects that are ERAP1 reference that have an increased risk of developing uveitis, such as anterior uveitis, acute anterior uveitis, iridocyclitis, iritis, and pan-uveitis, may be treated such that the uveitis is prevented, the symptoms thereof are reduced, and/or development of symptoms is repressed. Accordingly, the present disclosure provides methods of leveraging the identification of such variants in subjects to identify or stratify risk in such subjects of developing uveitis, such as anterior uveitis, acute anterior uveitis, iridocyclitis, iritis, and pan-uveitis, or to diagnose subjects as having an increased risk of developing uveitis, such as anterior uveitis, acute anterior uveitis, iridocyclitis, iritis, and pan-uveitis, such that subjects at risk or subjects with active disease may be treated accordingly.

For purposes of the present disclosure, any particular subject can be categorized as having one of three ERAP1 genotypes: i) ERAP1 reference; ii) heterozygous for an ERAP1 variant nucleic acid molecule; or iii) homozygous for an ERAP1 variant nucleic acid molecule. A subject is ERAP1 reference when the subject does not have a copy of an ERAP1 variant nucleic acid molecule. A subject is heterozygous for an ERAP1 variant nucleic acid molecule when the subject has a single copy of an ERAP1 variant nucleic acid molecule. As used herein, an ERAP1 variant nucleic acid molecule is any ERAP1 nucleic acid molecule (such as, a genomic nucleic acid molecule, an mRNA molecule, or a cDNA molecule) encoding an ERAP1 polypeptide having a partial loss-of-function, a complete loss-of-function, a predicted partial loss-of-function, or a predicted complete loss-of-function, or any ERAP1 nucleic acid molecule that results in decreased expression of ERAP1 polypeptide. A subject who has an ERAP1 variant nucleic acid molecule is hypomorphic for ERAP1. The ERAP1 variant nucleic acid molecule encoding an ERAP1 predicted loss-of-function polypeptide can be any nucleic acid molecule encoding an ERAP1 Lys528Arg or Asp575Asn. In some embodiments, the ERAP1 variant nucleic acid molecule encodes ERAP1 Lys528Arg. In some embodiments, the ERAP1 variant nucleic acid molecule encodes ERAP1 Asp575Asn. A subject is homozygous for an ERAP1 variant nucleic acid molecule when the subject has two copies of an ERAP1 variant nucleic acid molecule.

For subjects that are genotyped or determined to be ERAP1 reference, such subjects have an increased risk of developing uveitis, such as anterior uveitis, acute anterior uveitis, iridocyclitis, iritis, and pan-uveitis. For subjects that are genotyped or determined to be either ERAP1 reference or heterozygous for an ERAP1 variant nucleic acid molecule, such subjects can be treated with an ERAP1 inhibitor.

In some embodiments, subjects that are genotyped or determined to be ERAP1 reference have an even higher risk of developing uveitis, such as anterior uveitis, acute anterior uveitis, iridocyclitis, iritis, and pan-uveitis, when they also have an increased number of HLA-B27 alleles (such as one or two HLA-B27 alleles compared to no HLA-27 alleles). In some embodiments, subjects that are genotyped or determined to be heterozygous for an ERAP1 variant nucleic acid molecule also have an even higher risk of developing uveitis, such as anterior uveitis, acute anterior uveitis, iridocyclitis, iritis, and pan-uveitis, when they also have an increased number of HLA-B27 alleles (such as one or two HLA-B27 alleles compared to no HLA-27 alleles). In some embodiments, the subject may have one HLA-B27 allele and one HLA-B40 allele (and also be ERAP1 reference or heterozygous for an ERAP1 variant nucleic acid molecule) and have an even higher risk of developing uveitis, such as anterior uveitis, acute anterior uveitis, iridocyclitis, iritis, and pan-uveitis (compared to a similar subject but having no HLA-B27 alleles).

In any of the embodiments described throughout the present disclosure, the ERAP1 variant nucleic acid molecule can be any ERAP1 nucleic acid molecule (such as, for example, genomic nucleic acid molecule, mRNA molecule, or cDNA molecule) encoding an ERAP1 polypeptide having a partial loss-of-function, a complete loss-of-function, a predicted partial loss-of-function, or a predicted complete loss-of-function, or any ERAP1 nucleic acid molecule that results in decreased expression of ERAP1 polypeptide. In any of the embodiments described herein, the ERAP1 variant nucleic acid molecule can be any nucleic acid molecule (such as, a genomic nucleic acid molecule, an mRNA molecule, or a cDNA molecule) that is a missense variant, a splice-site variant, a stop-gain variant, a start-loss variant, a stop-loss variant, a frameshift variant, an in-frame indel variant, or a variant that encodes a truncated ERAP1 polypeptide. For example, the ERAP1 variant nucleic acid molecule can be any nucleic acid molecule encoding ERAP1 Lys528Arg. In some embodiments, the ERAP1 variant nucleic acid molecule encodes ERAP1 Asp575Asn. In some embodiments, the ERAP1 variant nucleic acid molecule is not rs30187.

In any of the embodiments described throughout the present disclosure, the ERAP1 predicted loss-of-function polypeptide can be any ERAP1 polypeptide having a partial loss-of-function, a complete loss-of-function, a predicted partial loss-of-function, or a predicted complete loss-of-function. In any of the embodiments described throughout the present disclosure, the ERAP1 predicted loss-of-function polypeptide can be any of the ERAP1 polypeptides described herein including, for example, ERAP1 Lys528Arg or Asp575Asn. In some embodiments, the ERAP1 predicted loss-of-function polypeptide is ERAP1 Lys528Arg. In some embodiments, the ERAP1 predicted loss-of-function polypeptide is ERAP1 Asp575Asn.

In any of the embodiments described throughout the present disclosure, the uveitis is anterior uveitis, acute anterior uveitis, iridocyclitis, iritis, or pan-uveitis. In any of the embodiments described throughout the present disclosure, the uveitis is anterior uveitis. In any of the embodiments described throughout the present disclosure, the uveitis is acute anterior uveitis. In any of the embodiments described throughout the present disclosure, the anterior uveitis includes iridocyclitis. In any of the embodiments described throughout the present disclosure, the anterior uveitis includes iritis. In any of the embodiments described throughout the present disclosure, the uveitis is pan-uveitis. In any of the embodiments described throughout the present disclosure, the subject can have ankylosing spondylitis. In any of the embodiments described throughout the present disclosure, the subject does not have ankylosing spondylitis.

Symptoms of an anterior uveitis include, but are not limited to, severe redness in the eye, pain, dark floating spots in one's vision (so-called called "floaters"), light sensitivity, and or blurred vision.

The present disclosure provides methods of treating a subject having uveitis, the method comprising administering an ERAP1 inhibitor to the subject. In some embodiments, the uveitis is anterior uveitis. In some embodiments, the uveitis is acute anterior uveitis. In some embodiments, the uveitis is pan-uveitis.

The present disclosure also provides methods of treating a subject having iridocyclitis, the methods comprising administering an ERAP1 inhibitor to the subject.

The present disclosure also provides methods of treating a subject having iritis, the methods comprising administering an ERAP1 inhibitor to the subject.

In some embodiments, the ERAP1 inhibitor comprises an inhibitory nucleic acid molecule. In some embodiments, the inhibitory nucleic acid molecule comprises an antisense molecule, a small interfering RNA (siRNA) molecule, or a short hairpin RNA (shRNA) molecule. In some embodiments, the inhibitory nucleic acid molecule comprises an antisense molecule. In some embodiments, the inhibitory nucleic acid molecule comprises an siRNA molecule. In some embodiments, the inhibitory nucleic acid molecule comprises an shRNA molecule. Such inhibitory nucleic acid molecules can be designed to target any region of an ERAP1 nucleic acid molecule, such as an mRNA molecule. In some embodiments, the inhibitory nucleic acid molecule hybridizes to a sequence within an ERAP1 genomic nucleic acid molecule or mRNA molecule and decreases expression of the ERAP1 polypeptide in a cell in the subject. In some embodiments, the ERAP1 inhibitor comprises an antisense RNA that hybridizes to an ERAP1 genomic nucleic acid molecule or mRNA molecule and decreases expression of the ERAP1 polypeptide in a cell in the subject. In some embodiments, the ERAP1 inhibitor comprises an siRNA that hybridizes to an ERAP1 genomic nucleic acid molecule or mRNA molecule and decreases expression of the ERAP1 polypeptide in a cell in the subject. In some embodiments, the ERAP1 inhibitor comprises an shRNA that hybridizes to an ERAP1 genomic nucleic acid molecule or mRNA molecule and decreases expression of the ERAP1 polypeptide in a cell in the subject.

In some embodiments, the ERAP1 antisense nucleic acid molecules comprise or consist of any of the nucleotide sequences represented by SEQ ID NOs: 35-784. In some embodiments, the ERAP1 siRNA molecules comprise or consist of any of the nucleotide sequences (sense and antisense strands presented one after the other) represented by SEQ ID NOs: 785-2578 (e.g., the sense strand is, for example, SEQ ID NO: 785 and the corresponding antisense strand is SEQ ID NO: 786; the sense strand is, for example, SEQ ID NO: 787 and the corresponding antisense strand is SEQ ID NO: 788; etc.).

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/ i2FN/mN/i2FN/mN/i2FN/mN/i2FN/*mN*/32FN/
Antisense: /52FN/*/i2FN/*mN/i2FN/mN/i2FN/mN/i2FN/ mN/i2FN/mN/i2FN/mN/i2FN/mN/i2FN/mN/i2FN/ mN*N*N wherein: "N" is the base; "2F" is a 2'-F modification; "m" is a 2'-O-methyl modification, "I" is an internal base; and "*" is a phosphorothioate backbone linkage.

In any of the embodiments described herein, the inhibitory nucleic acid molecules may be administered, for example, as one to two hour i.v. infusions or s.c. injections. In any of the embodiments described herein, the inhibitory nucleic acid molecules may be administered at dose levels that range from about 50 mg to about 900 mg, from about 100 mg to about 800 mg, from about 150 mg to about 700 mg, or from about 175 to about 640 mg (2.5 to 9.14 mg/kg; 92.5 to 338 mg/m$^2$-based on an assumption of a body weight of 70 kg and a conversion of mg/kg to mg/m$^2$ dose levels based on a mg/kg dose multiplier value of 37 for humans).

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the ERAP1 inhibitor comprises a nuclease agent that induces one or more nicks or double-strand breaks at a recognition sequence(s) or a DNA-binding protein that binds to a recognition sequence within an ERAP1 genomic nucleic acid molecule. The recognition sequence can be located within a coding region of the ERAP1 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the ERAP1 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30 to about 36 bp for a zinc finger protein or ZFN pair, about 15 to about 18 bp for each ZFN, about 36 bp for a TALE protein or TALEN, and about 20 bp for a CRISPR/Cas guide RNA.

In some embodiments, CRISPR/Cas systems can be used to modify an ERAP1 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of ERAP1 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an ERAP1 genomic nucleic acid molecule or it can be a nickase that creates a single-strand break in an ERAP1 genomic nucleic acid molecule. Additional examples of Cas proteins include, but are not limited to, Cas1, Cas1B, Cast, Cas3, Cas4, Cas5, Cas5e (CasD), Casio, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of an ERAP1 genomic nucleic acid molecules can be generated by contacting a cell with a Cas protein and one or more gRNAs that hybridize to one or more gRNA recognition sequences within a target genomic locus in the ERAP1 genomic nucleic acid molecule. For example, a gRNA recognition sequence can be located within a region of SEQ ID NO:1. The gRNA recognition sequence can also include or be proximate to a position corresponding to: position 19,474, position 21,595, position 21,811, or position 42,579. For example, the gRNA recognition sequence can be located about 1000, about 500, about 400, about 300, about 200, about 100, about 50, about 45, about 40, about 35, about 30, about 25, about 20, about 15, about 10, or about 5 nucleotides from a position corresponding to: position 19,474, position 21,595, position 21,811, or position 42,579. The gRNA recognition sequence can include or be proximate to the start codon or the stop codon of an ERAP1 genomic nucleic acid molecule. For example, the gRNA recognition sequence can be located about 10, about 20, about 30, about 40, about 50, about 100, about 200, about 300, about 400, about 500, or about 1,000 nucleotides from the start codon or the stop codon.

The gRNA recognition sequences within a target genomic locus in an ERAP1 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes a PAM. In addition, 5'-NGA-3' can be a highly efficient non-canonical PAM for human cells. Generally, the PAM is about 2 to about 6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10 base pairs, about 2 to about 5 base pairs, or 3 base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an ERAP1 genomic nucleic acid molecule. An exemplary gRNA is a gRNA effective to direct a Cas enzyme to bind to or cleave an ERAP1 genomic nucleic acid molecule, wherein the gRNA comprises a DNA-targeting segment that hybridizes to a gRNA recognition sequence within the ERAP1 genomic nucleic acid molecule that includes or is proximate to a position corresponding to: position 19,474, position 21,595, position 21,811, or position 42,579. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from a position corresponding to: position 19,474, position 21,595, position 21,811, or position 42,579. Other exemplary gRNAs comprise a DNA-targeting segment that hybridizes to a gRNA recognition sequence present within an ERAP1 genomic nucleic acid molecule that includes or is proximate to the start codon or the stop codon. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from the start codon or located about 5, about 10, about 15, about 20, about 25, about 30, about 35, about 40, about 45, about 50, about 100, about 200, about 300, about 400, about 500, or about 1,000 nucleotides from the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs comprise 20 nucleotides.

Examples of suitable gRNA recognition sequences located within the ERAP1 reference gene are set forth in Table 1 as SEQ ID NOs:15-34.

TABLE 1

Guide RNA Recognition Sequences Near ERAP1 Variation(s)

| Strand | gRNA Recognition Sequence | SEQ ID NO: |
|---|---|---|
| + | GTGCAATTTGCTCCTGACGG | 15 |
| + | CACTTG CCATACTATCCCAC | 16 |
| + | TGTACGGGAGCCCGACAAGG | 17 |
| − | GAAGATGAGCACCTATCTGG | 18 |
| − | CCCTAATAACCATCACAGTG | 19 |
| + | AAGGCCATTCTAGCTGCAGT | 20 |
| − | AGATTATGCACTGGATGCTG | 21 |
| + | CAAAAATCGATGGACCATGT | 22 |
| + | TTTCCACAGGTGTAGACACA | 23 |
| − | TGAAAACCATGATGAACACT | 24 |
| + | CATAGCACCAGACTGAAAGT | 25 |
| + | TCAAGAGATCATAATGAACT | 26 |
| − | TTGTATTCTGAATATGCTAA | 27 |
| − | GAAGCAAGAGCACTACATGA | 28 |
| − | ACCTGGTCACTATGGAATGG | 29 |
| − | CAAAAGCACCTACAGAACCA | 30 |
| + | CTGTGTACGGGAGCCCGACA | 31 |
| − | ATACAAAAACGAGGACCTG | 32 |
| + | TCCACCATTCCATAGTGACC | 33 |
| − | CTATTACATTGTGCATTACG | 34 |

The Cas protein and the gRNA form a complex, and the Cas protein cleaves the target ERAP1 genomic nucleic acid molecule. The Cas protein can cleave the nucleic acid molecule at a site within or outside of the nucleic acid sequence present in the target ERAP1 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the ERAP1 genomic nucleic acid molecule to which a DNA-targeting segment of a gRNA will bind.

Such methods can result, for example, in an ERAP1 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the ERAP1 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the ERAP1 inhibitor comprises a small molecule degrader, a proteoloysis-targeting chimera, or an immunomodulatory agent. In some embodiments, the ERAP1 inhibitor comprises an anti-ERAP1 antibody. In some embodiments, the ERAP1 inhibitor is DG002 and DG013 (see, Zervoudi et al., Proc. Nat'l Acad. Sci. USA, 2013, 110, 19890-19895). In some embodiments, the ERAP1 inhibitor is a phosphinic dipeptide or tripeptide analog (see, Weglarz-Tomczak et al., Bioorg. Med. Chem. Lett., 2016, 26, 4122-4126). In some embodiments, the ERAP1 inhibitor is (N—(N-(2-(1H-indol-3-yl)ethyl) carbamimidoyl)-2,5-difluorobenzenesulfonamide), (1-(1-(4-acetylpiperazine-1-carbonyl) cyclohexyl)-3-(p-tolyl)urea), or (4-methoxy-3-(N-(2-(piperidin-1-yl)-5-(trifluoromethyl) phenyl)sulfamoyl)benzoic acid (see, Maben et al., J. Med. Chem., 2020, 63, 103-121). In some embodiments, the ERAP1 inhibitor is (4aR,5S,6R,8S,8aR)-5-(2-(Furan-3-yl) ethyl)-8-hydroxy-5,6,8a-trimethyl-3,4,4a,5,6,7,8,8a-octahydronaphthalene-1-carboxylic acid (see, Liddle et al., J. Med. Chem., 2020, 63, 3348-3358). In some embodiments, the ERAP1 inhibitor is DG013A or a phosphinic tripeptide or dipeptide or an aminophosphonic derivative, or 3,4-diaminobenzoic (DABA) derivative, or a derivative of thimerosal, (see, Georgiadis et al., Cur. Med. Chem., 2019, 26, 2715-2729). In some embodiments, the ERAP1 inhibitor is a benzofuran or 7-Benzofuran amide variation (see, Deddouche-Grass et al., ACS Med. Chem. Lett., 2021, 12, 1137-1142).

In some embodiments, the methods of treatment further comprise detecting the presence or absence of an ERAP1 variant nucleic acid molecule in a biological sample obtained from the subject. As used throughout the present disclosure, "an ERAP1 variant nucleic acid molecule" is any ERAP1 nucleic acid molecule (such as, for example, genomic nucleic acid molecule, mRNA molecule, or cDNA molecule) encoding an ERAP1 polypeptide having a partial loss-of-function, a complete loss-of-function, a predicted partial loss-of-function, or a predicted complete loss-of-function, or any ERAP1 nucleic acid molecule resulting in decreased expression of ERAP1 polypeptide.

The present disclosure also provides methods of treating a subject with a therapeutic agent that treats or inhibits uveitis. In some embodiments, the subject has uveitis, such as anterior uveitis. In some embodiments, the subject is at risk of developing uveitis, such as anterior uveitis. In some embodiments, the methods comprise determining whether the subject has an ERAP1 variant nucleic acid molecule by obtaining or having obtained a biological sample obtained from the subject, and performing or having performed a sequence analysis on the biological sample to determine if the subject has a genotype comprising the ERAP1 variant nucleic acid molecule. When the subject is ERAP1 reference, the therapeutic agent that treats or inhibits uveitis is administered or continued to be administered to the subject in a standard dosage amount, and/or an ERAP1 inhibitor is administered to the subject. When the subject is heterozygous for an ERAP1 variant nucleic acid molecule, the therapeutic agent that treats or inhibits uveitis is administered or continued to be administered to the subject in an amount that is the same as or less than a standard dosage amount, and/or an ERAP1 inhibitor is administered to the subject. The presence of a genotype having the ERAP1 variant nucleic acid molecule indicates the subject has a decreased risk of developing uveitis. In some embodiments, the subject is ERAP1 reference. In some embodiments, the subject is heterozygous for the ERAP1 variant nucleic acid molecule.

For subjects that are genotyped or determined to be either ERAP1 reference or heterozygous for the ERAP1 variant nucleic acid molecule, such subjects can be treated with an ERAP1 inhibitor, as described herein.

Detecting the presence or absence of an ERAP1 variant nucleic acid molecule in a biological sample obtained from a subject and/or determining whether a subject has an ERAP1 variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the ERAP1 variant nucleic acid molecule can be present within a cell obtained from the subject.

In some embodiments, when the subject is ERAP1 reference, the subject is also administered a therapeutic agent that treats or inhibits uveitis in a standard dosage amount. In some embodiments, when the subject is heterozygous for an ERAP1 variant nucleic acid molecule, the subject is also administered a therapeutic agent that treats or inhibits uveitis in a dosage amount that is the same as or less than a standard dosage amount.

In some embodiments, the treatment methods further comprise detecting the presence or absence of an ERAP1 predicted loss-of-function polypeptide in a biological sample obtained from the subject. In some embodiments, when the subject does not have an ERAP1 predicted loss-of-function polypeptide, the subject is also administered a therapeutic agent that treats or inhibits uveitis in a standard dosage amount. In some embodiments, when the subject has an ERAP1 predicted loss-of-function polypeptide, the subject is also administered a therapeutic agent that treats or inhibits uveitis in a dosage amount that is the same as or less than a standard dosage amount.

The present disclosure also provides methods of treating a subject with a therapeutic agent that treats or inhibits uveitis. In some embodiments, the subject has uveitis, such as anterior uveitis. In some embodiments, the subject is at risk of developing uveitis, such as anterior uveitis. In some embodiments, the methods comprise determining whether the subject has an ERAP1 predicted loss-of-function polypeptide by obtaining or having obtained a biological sample from the subject, and performing or having performed an assay on the biological sample to determine if the subject has an ERAP1 predicted loss-of-function polypeptide. When the subject does not have an ERAP1 predicted loss-of-function polypeptide, the therapeutic agent that treats or inhibits uveitis is administered or continued to be administered to the subject in a standard dosage amount, and/or an ERAP1 inhibitor is administered to the subject. When the subject has an ERAP1 predicted loss-of-function polypeptide, the therapeutic agent that treats or inhibits uveitis is administered or continued to be administered to the subject in an amount that is the same as or less than a standard dosage amount, and/or an ERAP1 inhibitor is administered to the subject. The presence of an ERAP1 predicted loss-of-function polypeptide indicates the subject has a decreased risk of developing uveitis. In some embodiments, the subject has an ERAP1 predicted loss-of-function polypeptide. In some embodiments, the subject does not have an ERAP1 predicted loss-of-function polypeptide.

Detecting the presence or absence of an ERAP1 predicted loss-of-function polypeptide in a biological sample obtained from a subject and/or determining whether a subject has an ERAP1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the ERAP1 predicted loss-of-function polypeptide can be present within a cell obtained from the subject.

Examples of therapeutic agents that treat or inhibit uveitis, such as anterior uveitis, include, but are not limited to: ophthalmic steroids, such as prednisolone, prednisone, difluprednate, triamcinolone acetonide, fluorometholone, fluocinolone, or dexamethasone; immunosuppressants, such as azathioprine and cyclophosphamide; glucocorticoids, such as cortisone; and antirheumatics, such as adalimumab. Additional therapeutic agents that treat or inhibit uveitis include, but are not limited to, cyclopentolate, atropine, homatropine, corticotropin, gentamicin, corticotropin, loteprednol, tobramycin, atropine, sulfasalazine, hydrocortisone, neomycin, polymyxin b, bacitracin, and sulfacetamide sodium.

In some embodiments, the dose of the therapeutic agents that treat or inhibit uveitis can be reduced by about 10%, by about 20%, by about 30%, by about 40%, by about 50%, by about 60%, by about 70%, by about 80%, or by about 90% for subjects that are heterozygous for an ERAP1 variant nucleic acid molecule (i.e., less than the standard dosage amount) compared to subjects that are ERAP1 reference (who may receive a standard dosage amount). In some embodiments, the dose of the therapeutic agents that treat or inhibit uveitis can be reduced by about 10%, by about 20%, by about 30%, by about 40%, or by about 50%. In addition, the dose of therapeutic agents that treat or inhibit uveitis in subjects that are heterozygous for an ERAP1 variant nucleic acid molecule can be administered less frequently compared to subjects that are ERAP1 reference.

Administration of the therapeutic agents that treat or inhibit uveitis and/or ERAP1 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more. In addition, the therapeutic agents that treat or inhibit uveitis and/or ERAP1 inhibitors can be administered sequentially or at the same time. In addition, the therapeutic agents that treat or inhibit uveitis and/or ERAP1 inhibitors can be administered in separate compositions or can be administered together in the same composition.

Administration of the therapeutic agents that treat or inhibit uveitis and/or ERAP1 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in uveitis, a decrease/reduction in the severity of uveitis (such as, for example, a reduction or inhibition of development of anterior uveitis), a decrease/reduction in symptoms and uveitis-related effects, delaying the onset of symptoms of uveitis-related effects, reducing the severity of symptoms of uveitis-related effects, reducing the severity of an acute episode, reducing the number of symptoms of uveitis-related effects, reducing the latency of symptoms of uveitis-related effects, an amelioration of symptoms of uveitis-related effects, reducing secondary symptoms, reducing secondary infections, preventing relapse to uveitis, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of any therapeutic agent or composition. A prophylactic effect may comprise a complete or partial avoidance/inhibition or a delay of uveitis development/progression (such as, for example, a complete or partial avoidance/inhibition or a delay), and an increased survival time of the affected host animal, following administration of a therapeutic protocol. Treatment of uveitis encompasses the treatment of subjects already diagnosed as having any form of uveitis at any clinical stage or manifestation, the delay of the onset or evolution or aggravation or deterioration of the symptoms or signs of uveitis, and/or preventing and/or reducing the severity of uveitis.

The present disclosure also provides methods of identifying a subject having an increased risk of developing uveitis, such as anterior uveitis. In some embodiments, the methods comprise determining or having determined the presence or absence of an ERAP1 variant nucleic acid molecule (such as a genomic nucleic acid molecule, mRNA molecule, and/or cDNA molecule) in a biological sample obtained from the subject. When the subject lacks an ERAP1 variant nucleic acid molecule (i.e., the subject is genotypically categorized as ERAP1 reference), then the subject has an increased risk of developing uveitis, such as anterior uveitis. When the subject has an ERAP1 variant nucleic acid molecule (i.e., the subject is heterozygous or homozygous for an ERAP1 variant nucleic acid molecule), then the subject has a decreased risk of developing uveitis compared to a subject that is ERAP1 reference.

Having a single copy of an ERAP1 variant nucleic acid molecule is more protective of a subject from developing uveitis than having no copies of an ERAP1 variant nucleic acid molecule. Without intending to be limited to any particular theory or mechanism of action, it is believed that a single copy of an ERAP1 variant nucleic acid molecule (i.e., heterozygous for an ERAP1 variant nucleic acid molecule) is protective of a subject from developing uveitis, such as anterior uveitis, and it is also believed that having two copies of an ERAP1 variant nucleic acid molecule (i.e., homozygous for an ERAP1 variant nucleic acid molecule) may be more protective of a subject from developing uveitis, such as anterior uveitis, relative to a subject with a single copy. Thus, in some embodiments, a single copy of an ERAP1 variant nucleic acid molecule may not be completely protective, but instead, may be partially or incompletely protective of a subject from developing uveitis, such as anterior uveitis. While not desiring to be bound by any particular theory, there may be additional factors or molecules involved in the development of uveitis that are still present in a subject having a single copy of an ERAP1 variant nucleic acid molecule, thus resulting in less than complete protection from the development of uveitis.

Detecting the presence or absence of an ERAP1 variant nucleic acid molecule in a biological sample obtained from a subject and/or determining whether a subject has an ERAP1 variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the ERAP1 variant nucleic acid molecule can be present within a cell obtained from the subject.

In some embodiments, when a subject is identified as having an increased risk of developing uveitis, the subject is further treated with a therapeutic agent that treats or inhibits uveitis and/or an ERAP1 inhibitor, as described herein. For example, when the subject is ERAP1 reference, and therefore has an increased risk for developing uveitis, the subject is administered an ERAP1 inhibitor. In some embodiments, such a subject is also administered a therapeutic agent that treats or inhibits uveitis. In some embodiments, when the subject is heterozygous for an ERAP1 variant nucleic acid molecule, the subject is administered the therapeutic agent that treats or inhibits uveitis in a dosage amount that is the same as or less than a standard dosage amount, and is also administered an ERAP1 inhibitor. In some embodiments, the subject is ERAP1 reference. In some embodiments, the subject is heterozygous for an ERAP1 variant nucleic acid molecule.

In any of the methods described herein, the methods can further comprise detecting the presence or absence of HLA-B27 and/or HLA-B40 in a biological sample obtained from the subject. In some embodiments, the subject is or is suspected of being HLA-B27$^+$. In some embodiments, the subject is or is suspected of being HLA-B40$^+$. In some embodiments, the method further comprises determining whether the subject has one or two copies of HLA-B27 and/or HLA-B40. In some embodiments, the subject has a single copy of HLA-B27 or HLA-B40. In some embodiments, the subject has two copies of HLA-B27 or HLA-B40. In some embodiments, the subject has a single copy of HLA-B27 and a single copy of HLA-B40. In some embodiments, the method further comprises administering to the subject an HLA-B27 inhibitor or an HLA-B40 inhibitor. In some embodiments, the HLA-B27 inhibitor or HLA-B40 inhibitor is an antibody. In some embodiments, the antibody is an anti-HLA-B27 antibody or an anti-HLA-B40 antibody. In some embodiments, the HLA-B27 inhibitor or HLA-B40 inhibitor comprises a small molecule degrader or an inhibitory nucleic acid molecule. In some embodiments, the inhibitory nucleic acid molecule is an antisense nucleic acid molecule, an siRNA, or an shRNA that hybridizes to an HLA-B27 or an HLA-B40.

In some embodiments, the B27 antisense nucleic acid molecules comprise or consist of any of the nucleotide sequences represented by SEQ ID NOs: 2579-2923. In some embodiments, the B27 siRNA molecules comprise or consist of any of the nucleotide sequences (sense and antisense strands presented one after the other) represented by SEQ ID NOs: 2924-3661 (e.g., the sense strand is, for example, SEQ ID NO: 2924 and the corresponding antisense strand is SEQ ID NO: 2925; the sense strand is, for example, SEQ ID NO: 2926 and the corresponding antisense strand is SEQ ID NO: 2927; etc.).

HLA-class-I antibodies can be generated by numerous methodologies with different degrees of antigen/allele specificity attained and are reported to be used for in vitro assays. HLA-B27 antibodies can be generated by numerous methodologies. In addition, three commercially available antibodies for HLA-B27 flow cytometric screening include the monoclonal mouse anti-human ABC-m3, FD705, and GS145.2 which have been shown to each have differing levels of cross-reactivity to other HLA-B antigens/alleles (Levering et al., Cytometry B Clin. Cytom., 2003, 54, 28-38).

The present disclosure also provides methods of detecting the presence or absence of an ERAP1 variant genomic nucleic acid molecule in a biological sample obtained from a subject, and/or an ERAP1 variant mRNA molecule in a biological sample obtained from a subject, and/or an ERAP1 variant cDNA molecule produced from an mRNA molecule in a biological sample obtained from a subject. It is understood that gene sequences within a population and mRNA molecules encoded by such genes can vary due to polymorphisms such as SNPs. The sequences provided herein for the ERAP1 variant genomic nucleic acid molecules, ERAP1 variant mRNA molecules, and ERAP1 variant cDNA molecules are only exemplary sequences. Other sequences for the ERAP1 variant genomic nucleic acid molecules, variant mRNA molecules, and variant cDNA molecules are also possible.

The biological sample can be derived from any cell, tissue, or biological fluid from the subject. The biological sample may comprise any clinically relevant tissue such as, for example, a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the biological sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any ERAP1 variant nucleic acid molecule, preliminary processing designed to isolate or enrich the biological sample for the ERAP1 variant nucleic acid molecule can be employed. A variety of techniques may be used for this purpose. When detecting the level of any ERAP1 variant mRNA molecule, different techniques can be used enrich the biological sample with mRNA molecules. Various methods to detect the presence or level of an mRNA molecule or the presence of a particular variant genomic DNA locus can be used.

The present disclosure also provides methods of detecting an ERAP1 variant nucleic acid molecule, or the complement thereof, in a subject. The methods comprise assaying a biological sample obtained from the subject to determine whether a nucleic acid molecule in the biological sample is an ERAP1 variant nucleic acid molecule.

In some embodiments, the ERAP1 variant nucleic acid molecule, or the complement thereof, is a genomic nucleic acid molecule having a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement.

In some embodiments, the ERAP1 variant nucleic acid molecule, or the complement thereof, is an mRNA molecule having a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof.

In some embodiments, the ERAP1 variant nucleic acid molecule, or the complement thereof, is a cDNA molecule produced from an mRNA molecule in the biological sample having a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

In some embodiments, the ERAP1 variant nucleic acid molecule has a nucleotide sequence comprising: a guanine at a position corresponding to position 19,474 according to SEQ ID NO:2, or the complement thereof, (for genomic nucleic acid molecules); a guanine at a position corresponding to position 1,841 according to SEQ ID NO:7, or the complement thereof, (for mRNA molecules); or a guanine at a position corresponding to position 1,841 according to SEQ ID NO:10, or the complement thereof, (for cDNA molecules obtained from mRNA molecules).

In some embodiments, the ERAP1 variant nucleic acid molecule has a nucleotide sequence comprising: an adenine at a position corresponding to position 21,595 according to SEQ ID NO:3, or the complement thereof, (for genomic nucleic acid molecules); an adenine at a position corresponding to position 1,981 according to SEQ ID NO:8, or the complement thereof, (for mRNA molecules); or an adenine at a position corresponding to position 1,981 according to SEQ ID NO:11, or the complement thereof, (for cDNA molecules obtained from mRNA molecules).

In some embodiments, the ERAP1 variant nucleic acid molecule has a nucleotide sequence comprising a cytosine at a position corresponding to position 21,811 according to SEQ ID NO:4, or the complement thereof.

In some embodiments, the ERAP1 variant nucleic acid molecule has a nucleotide sequence comprising a thymine at a position corresponding to position 42,579, or the complement thereof.

In some embodiments, the biological sample comprises a cell or cell lysate. Such methods can further comprise, for example, obtaining a biological sample from the subject comprising an ERAP1 genomic nucleic acid molecule or mRNA molecule, and if mRNA, optionally reverse transcribing the mRNA into cDNA. Such assays can comprise, for example determining the identity of these positions of the particular ERAP1 nucleic acid molecule. In some embodiments, the method is an in vitro method.

In some embodiments, the assay comprises sequencing at least a portion of the nucleotide sequence of the ERAP1 nucleic acid molecule, or the complement thereof, in the biological sample. In some embodiments, the assay comprises sequencing at least a portion of: the nucleotide sequence of the ERAP1 genomic nucleic acid molecule in the biological sample, wherein the sequenced portion comprises a position corresponding to position 19,474 according to SEQ ID NO:2, or the complement thereof; the nucleotide sequence of the ERAP1 mRNA molecule in the biological sample, wherein the sequenced portion comprises a position corresponding to position 1,841 according to SEQ ID NO:7, or the complement thereof; and/or the nucleotide sequence of the ERAP1 cDNA molecule produced from the mRNA in the biological sample, wherein the sequenced portion comprises a position corresponding to position 1,841 according to SEQ ID NO:10, or the complement thereof. When the sequenced portion of the ERAP1 nucleic acid molecule in the biological sample comprises: a guanine at a position corresponding to position 19,474 according to SEQ ID NO:2, or the complement thereof; a guanine at a position corresponding to position 1,841 according to SEQ ID NO:7, or the complement thereof; or a guanine at a position corresponding to position 1,841 according to SEQ ID NO:10, or the complement thereof; then the ERAP1 nucleic acid molecule in the biological sample is an ERAP1 variant nucleic acid molecule.

In some embodiments, the assay comprises sequencing at least a portion of: the nucleotide sequence of the ERAP1 genomic nucleic acid molecule in the biological sample, wherein the sequenced portion comprises a position corresponding to position 21,595 according to SEQ ID NO:3, or the complement thereof; the nucleotide sequence of the ERAP1 mRNA molecule in the biological sample, wherein the sequenced portion comprises a position corresponding to position 1,981 according to SEQ ID NO:8, or the complement thereof; and/or the nucleotide sequence of the ERAP1 cDNA molecule produced from the mRNA in the biological sample, wherein the sequenced portion comprises a position corresponding to position 1,981 according to SEQ ID NO:11, or the complement thereof. When the sequenced portion of the ERAP1 nucleic acid molecule in the biological sample comprises: an adenine at a position corresponding to position 21,595 according to SEQ ID NO:3, or the complement thereof; an adenine at a position corresponding to position 1,981 according to SEQ ID NO:8, or the complement thereof; or an adenine at a position corresponding to position 1,981 according to SEQ ID NO:11, or the complement thereof; then the ERAP1 nucleic acid molecule in the biological sample is an ERAP1 variant nucleic acid molecule.

In some embodiments, the assay comprises sequencing at least a portion of: the nucleotide sequence of the ERAP1 genomic nucleic acid molecule in the biological sample, wherein the sequenced portion comprises a position corresponding to position 21,811 according to SEQ ID NO:4, or the complement thereof; then the ERAP1 nucleic acid molecule in the biological sample is an ERAP1 variant nucleic acid molecule.

In some embodiments, the assay comprises sequencing at least a portion of: the nucleotide sequence of the ERAP1 genomic nucleic acid molecule in the biological sample, wherein the sequenced portion comprises a position corresponding to position 42,579 according to SEQ ID NO:5, or the complement thereof; then the ERAP1 nucleic acid molecule in the biological sample is an ERAP1 variant nucleic acid molecule.

In some embodiments, the assay comprises sequencing at least a portion of the nucleotide sequence of the ERAP1 genomic nucleic acid molecule, or the complement thereof, in the biological sample, wherein the sequenced portion comprises a position corresponding to: position 19,474 according to SEQ ID NO:2, or the complement thereof; position 21,595 according to SEQ ID NO:3, or the complement thereof; position 21,811 according to SEQ ID NO:4, or the complement thereof; or position 42,579 according to SEQ ID NO:5, or the complement thereof. When the sequenced portion of the ERAP1 genomic nucleic acid molecule in the biological sample comprises: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; then the ERAP1 genomic nucleic acid molecule in the biological sample is an ERAP1 variant genomic nucleic acid molecule.

In some embodiments, the assay comprises sequencing at least a portion of the nucleotide sequence of the ERAP1 mRNA molecule in the biological sample, wherein the sequenced portion comprises a position corresponding to: position 1,841 according to SEQ ID NO:7, or the complement thereof; position 1,981 according to SEQ ID NO:8, or the complement thereof; then the ERAP1 mRNA molecule in the biological sample is an ERAP1 variant mRNA molecule.

In some embodiments, the assay comprises sequencing at least a portion of the nucleotide sequence of the ERAP1 cDNA molecule produced from an mRNA molecule in the biological sample, wherein the sequenced portion comprises a position corresponding to: position 1,841 according to SEQ ID NO:10, or the complement thereof; position 1,981 according to SEQ ID NO:11, or the complement thereof; then the ERAP1 cDNA molecule produced from an mRNA molecule in the biological sample is an ERAP1 variant cDNA molecule.

In some embodiments, the assay comprises: a) contacting the biological sample with a primer hybridizing to a portion of the nucleotide sequence of the ERAP1: genomic nucleic acid molecule, or the complement thereof, that is proximate to a position corresponding to position 19,474 according to SEQ ID NO:2, or the complement thereof; mRNA molecule, or the complement thereof, that is proximate to a position corresponding to position 1,841 according to SEQ ID NO:7, or the complement thereof; and/or cDNA molecule, or the complement thereof, that is proximate to a position corresponding to position 1,841 according to SEQ ID NO:10, or the complement thereof; b) extending the primer at least through the position of the nucleotide sequence of the ERAP1: genomic nucleic acid molecule, or the complement thereof, corresponding to position 19,474 according to SEQ ID NO:2, or the complement thereof; mRNA molecule, or the complement thereof, corresponding to position 1,841 according to SEQ ID NO:7, or the complement thereof; and/or cDNA molecule, or the complement thereof, corresponding to position 1,841 according to SEQ ID NO:10, or the complement thereof; and c) determining whether the extension product of the primer comprises: a guanine at a position corresponding to position 19,474 according to SEQ ID NO:2, or the complement thereof; a guanine at a position corresponding to position 1,841 according to SEQ ID NO:7, or the complement thereof; and/or a guanine at a position corresponding to position 1,841 according to SEQ ID NO:10, or the complement thereof.

In some embodiments, the assay comprises: a) contacting the biological sample with a primer hybridizing to a portion of the nucleotide sequence of the ERAP1: genomic nucleic acid molecule, or the complement thereof, that is proximate to a position corresponding to position 21,595 according to SEQ ID NO:3, or the complement thereof; mRNA molecule, or the complement thereof, that is proximate to a position corresponding to position 1,981 according to SEQ ID NO:8, or the complement thereof; and/or cDNA molecule, or the complement thereof, that is proximate to a position corresponding to position 1,981 according to SEQ ID NO:11, or the complement thereof; b) extending the primer at least through the position of the nucleotide sequence of the ERAP1: genomic nucleic acid molecule, or the complement thereof, corresponding to position 21,595 according to SEQ ID NO:3, or the complement thereof; mRNA molecule, or the complement thereof, corresponding to position 1,981 according to SEQ ID NO:8, or the complement thereof; and/or cDNA molecule, or the complement thereof, corresponding to position 1,981 according to SEQ ID NO:11, or the complement thereof; and c) determining whether the extension product of the primer comprises: an adenine at a position corresponding to position 21,595 according to SEQ ID NO:3, or the complement thereof; an adenine at a position corresponding to position 1,981 according to SEQ ID NO:8, or the complement thereof; and/or an adenine at a position corresponding to position 1,981 according to SEQ ID NO:11, or the complement thereof.

In some embodiments, the assay comprises: a) contacting the biological sample with a primer hybridizing to a portion of the nucleotide sequence of the ERAP1 genomic nucleic acid molecule, or the complement thereof, that is proximate to a position corresponding to position 21,811 according to SEQ ID NO:4, or the complement thereof; b) extending the primer at least through the position of the nucleotide sequence of the ERAP1: genomic nucleic acid molecule, or the complement thereof, corresponding to position 21,811 according to SEQ ID NO:4, or the complement thereof; and c) determining whether the extension product of the primer comprises: a cytosine at a position corresponding to position 21,811 according to SEQ ID NO:4, or the complement thereof.

In some embodiments, the assay comprises: a) contacting the biological sample with a primer hybridizing to a portion of the nucleotide sequence of the ERAP1 genomic nucleic acid molecule, or the complement thereof, that is proximate to a position corresponding to position 42,579 according to SEQ ID NO:5, or the complement thereof; b) extending the primer at least through the position of the nucleotide sequence of the ERAP1: genomic nucleic acid molecule, or the complement thereof, corresponding to position 42,579 according to SEQ ID NO:5, or the complement thereof; and c) determining whether the extension product of the primer comprises: a thymine at a position corresponding to position 42,579 according to SEQ ID NO:5, or the complement thereof.

In some embodiments, the assay comprises: a) contacting the biological sample with a primer hybridizing to a portion of the nucleotide sequence of the ERAP1 genomic nucleic acid molecule, or the complement thereof, that is proximate to a position corresponding to: position 19,474 according to SEQ ID NO:2, or the complement thereof; position 21,595 according to SEQ ID NO:3, or the complement thereof; position 21,811 according to SEQ ID NO:4, or the complement thereof; or position 42,579 according to SEQ ID NO:5, or the complement thereof; b) extending the primer at least through the position of the nucleotide sequence of the ERAP1 genomic nucleic acid molecule, or the complement thereof, corresponding to: position 19,474 according to SEQ ID NO:2, or the complement thereof; position 21,595 according to SEQ ID NO:3, or the complement thereof; position 21,811 according to SEQ ID NO:4, or the complement thereof; or position 42,579 according to SEQ ID NO:5, or the complement thereof; and c) determining whether the extension product of the primer comprises: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof.

In some embodiments, the assay comprises: a) contacting the biological sample with a primer hybridizing to a portion of the nucleotide sequence of the ERAP1 mRNA molecule, or the complement thereof, that is proximate to a position corresponding to: position 1,841 according to SEQ ID NO:7, or the complement thereof; or position 1,981 according to SEQ ID NO:8, or the complement thereof; b) extending the primer at least through the position of the nucleotide sequence of the ERAP1 mRNA molecule, or the complement thereof, corresponding to: position 1,841 according to SEQ ID NO:7, or the complement thereof; or position 1,981 according to SEQ ID NO:8, or the complement thereof; and c) determining whether the extension product of the primer comprises: a guanine at a position corresponding to position 1,841 according to SEQ ID NO:7, or the complement thereof; or an adenine at a position corresponding to position 1,981 according to SEQ ID NO:8, or the complement thereof.

In some embodiments, the assay comprises: a) contacting the biological sample with a primer hybridizing to a portion of the nucleotide sequence of the ERAP1 cDNA molecule, or the complement thereof, that is proximate to a position corresponding to: position 1,841 according to SEQ ID NO:10, or the complement thereof; or position 1,981 according to SEQ ID NO:11, or the complement thereof; b) extending the primer at least through the position of the nucleotide sequence of the ERAP1 cDNA molecule, or the complement thereof, corresponding to: position 1,841 according to SEQ ID NO:10, or the complement thereof; or position 1,981 according to SEQ ID NO:11, or the complement thereof; and c) determining whether the extension product of the primer comprises: a guanine at a position corresponding to position 1,841 according to SEQ ID NO:10, or the complement thereof; or an adenine at a position corresponding to position 1,981 according to SEQ ID NO:11, or the complement thereof.

In some embodiments, the assay comprises sequencing the entire nucleic acid molecule. In some embodiments, only an ERAP1 genomic nucleic acid molecule is analyzed. In some embodiments, only an ERAP1 mRNA is analyzed. In some embodiments, only an ERAP1 cDNA obtained from an ERAP1 mRNA is analyzed.

In some embodiments, the assay comprises: a) amplifying at least a portion of the ERAP1 nucleic acid molecule, or the complement thereof, in the biological sample, wherein the amplified portion comprises: a guanine at a position corresponding to position 19,474 according to SEQ ID NO:2, or the complement thereof; a guanine at a position corresponding to position 1,841 according to SEQ ID NO:7, or the complement thereof; and/or a guanine at a position corresponding to position 1,841 according to SEQ ID NO:10, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a guanine at a position corresponding to position 19,474 according to SEQ ID NO:2, or the complement thereof; a guanine at a position corresponding to position 1,841 according to SEQ ID NO:7, or the complement thereof; and/or a guanine at a position corresponding to position 1,841 according to SEQ ID NO:10, or the complement thereof; and d) detecting the detectable label.

In some embodiments, the assay comprises: a) amplifying at least a portion of the ERAP1 nucleic acid molecule, or the complement thereof, in the biological sample, wherein the amplified portion comprises: an adenine at a position corresponding to position 21,595 according to SEQ ID NO:3, or the complement thereof; an adenine at a position corresponding to position 1,981 according to SEQ ID NO:8, or the complement thereof; and/or an adenine at a position corresponding to position 1,981 according to SEQ ID NO:11, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: an adenine at a position corresponding to position 21,595 according to SEQ ID NO:3, or the complement thereof; an adenine at a position corresponding to position 1,981 according to SEQ ID NO:8, or the complement thereof; and/or an adenine at a position corresponding to position 1,981 according to SEQ ID NO:11, or the complement thereof; and d) detecting the detectable label.

In some embodiments, the assay comprises: a) amplifying at least a portion of the ERAP1 nucleic acid molecule, or the complement thereof, in the biological sample, wherein the amplified portion comprises: a cytosine at a position corresponding to position 21,811 according to SEQ ID NO:4, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a cytosine at a position corresponding to position 21,811 according to SEQ ID NO:4, or the complement thereof; and d) detecting the detectable label.

In some embodiments, the assay comprises: a) amplifying at least a portion of the ERAP1 nucleic acid molecule, or the complement thereof, in the biological sample, wherein the amplified portion comprises: a thymine at a position corresponding to position 42,579 according to SEQ ID NO:5, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a thymine at a position corresponding to position 42,579 according to SEQ ID NO:5, or the complement thereof; and d) detecting the detectable label.

In some embodiments, the assay comprises: a) amplifying at least a portion of the ERAP1 genomic nucleic acid molecule, or the complement thereof, in the biological sample, wherein the portion comprises: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; and d) detecting the detectable label.

In some embodiments, the assay comprises: a) amplifying at least a portion of the ERAP1 mRNA molecule, or the complement thereof, in the biological sample, wherein the portion comprises: a guanine at a position corresponding to position 1,841 according to SEQ ID NO:7, or the complement thereof; or an adenine at a position corresponding to position 1,981 according to SEQ ID NO:8, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a guanine at a position corresponding to position 1,841 according to SEQ ID NO:7, or the complement thereof; or an adenine at a position corresponding to position 1,981 according to SEQ ID NO:8, or the complement thereof; and d) detecting the detectable label.

In some embodiments, the assay comprises: a) amplifying at least a portion of the ERAP1 cDNA molecule, or the complement thereof, produced from an mRNA molecule in the biological sample, wherein the portion comprises: a guanine at a position corresponding to position 1,841 according to SEQ ID NO:10, or the complement thereof; or an adenine at a position corresponding to position 1,981 according to SEQ ID NO:11, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: a guanine at a position corresponding to position 1,841 according to SEQ ID NO:10, or the complement thereof; or an adenine at a position corresponding to position 1,981 according to SEQ ID NO:11, or the complement thereof; and d) detecting the detectable label.

In some embodiments, the nucleic acid molecule in the sample is mRNA and the mRNA is reverse-transcribed into cDNA prior to the amplifying step.

In some embodiments, the assay comprises: contacting the ERAP1 nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 nucleic acid molecule, or the complement thereof, comprising: a guanine at a position corresponding to position 19,474 according to SEQ ID NO:2, or the complement thereof; a guanine at a position corresponding to position 1,841 according to SEQ ID NO:7, or the complement thereof; and/or a guanine at a position corresponding to position 1,841 according to SEQ ID NO:10, or the complement thereof; and detecting the detectable label.

In some embodiments, the assay comprises: contacting the ERAP1 nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 nucleic acid molecule, or the complement thereof, comprising: an adenine at a position corresponding to position 21,595 according to SEQ ID NO:3, or the complement thereof; an adenine at a position corresponding to position 1,981 according to SEQ ID NO:8, or the complement thereof; and/or an adenine at a position corresponding to position 1,981 according to SEQ ID NO:11, or the complement thereof; and detecting the detectable label.

In some embodiments, the assay comprises: contacting the ERAP1 nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 nucleic acid molecule, or the complement thereof, comprising a cytosine at a position corresponding to position 21,811 according to SEQ ID NO:4, or the complement thereof; and detecting the detectable label.

In some embodiments, the assay comprises: contacting the ERAP1 nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 nucleic acid molecule, or the complement thereof, comprising a thymine at a position corresponding to position 42,579 according to SEQ ID NO:5, or the complement thereof; and detecting the detectable label.

In some embodiments, the assay comprises: contacting the ERAP1 genomic nucleic acid molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 genomic nucleic acid molecule, or the complement thereof, comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof; and detecting the detectable label.

In some embodiments, the assay comprises: contacting the ERAP1 mRNA molecule, or the complement thereof, in the biological sample with an alteration-specific probe comprising a detectable label, wherein the alteration-specific probe comprises a nucleotide sequence which hybridizes under stringent conditions to the nucleotide sequence of the ERAP1 mRNA molecule, or the complement thereof, comprising: a guanine at a position corresponding to position 1,841 according to SEQ ID NO:7, or the complement thereof; or an adenine at a position corresponding to position 1,981 according to SEQ ID NO:8, or the complement thereof; and detecting the detectable label.

In some embodiments, the assay comprises: contacting the ERAP1 cDNA molecule, or the complement thereof, produced from an mRNA molecule in the biological sample with an alteration-specific probe comprising a detectable label, wherein the alteration-specific probe comprises a nucleotide sequence which hybridizes under stringent conditions to the nucleotide sequence of the ERAP1 cDNA molecule, or the complement thereof, comprising: a guanine at a position corresponding to position 1,841 according to SEQ ID NO:10, or the complement thereof; or an adenine at a position corresponding to position 1,981 according to SEQ ID NO:11, or the complement thereof; and detecting the detectable label.

In some embodiments, the ERAP1 nucleic acid molecule is present within a cell obtained from the subject.

Alteration-specific polymerase chain reaction techniques can be used to detect mutations such as SNPs in a nucleotide sequence. Alteration-specific primers can be used because the DNA polymerase will not extend when a mismatch with the template is present.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an ERAP1 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether an ERAP1 nucleic acid molecule (genomic nucleic acid molecule, mRNA molecule, or cDNA molecule), or complement thereof, within a biological sample comprises a nucleotide sequence comprising a guanine at a position corresponding to position 19,474 according to SEQ ID NO:2 (genomic nucleic acid molecule), a guanine at a position corresponding to position 1,841 according to SEQ ID NO:7 (mRNA molecule), or a guanine at a position corresponding to position 1,841 according to SEQ ID NO:10 (cDNA molecule), the biological sample can be subjected to an amplification method using a primer pair that includes a first primer derived from the 5' flanking sequence adjacent to a guanine at a position corresponding to position 19,474 according to SEQ ID NO:2, a guanine at a position corresponding to position 1,841 according to SEQ ID NO:7, or a guanine at a position corresponding to position 1,841 according to SEQ ID NO:10, and a second primer derived from the 3' flanking sequence adjacent to a guanine at a position corresponding to position 19,474 according to SEQ ID NO:2, a guanine at a position corresponding to position 1,841 according to SEQ ID NO:7, or a guanine at a position corresponding to position 1,841 according to SEQ ID NO:10 to produce an amplicon that is indicative of the presence of the SNP at positions encoding a guanine at a position corresponding to position 19,474 according to SEQ ID NO:2, a guanine at a position corresponding to position 1,841 according to SEQ ID NO:7, or a guanine at a position corresponding to position 1,841 according to SEQ ID NO:10. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 19,474 according to SEQ ID NO:2, a guanine at a position corresponding to position 1,841 according to SEQ ID NO:7, or a guanine at a position corresponding to position 1,841 according to SEQ ID NO:10, and at least 1, 2, 3, 4, 5, 6, 7, 8, 9, 10, or more nucleotides on each side of positions comprising a guanine at a position corresponding to position 19,474 according to SEQ ID NO:2, a guanine at a position corresponding to position 1,841 according to SEQ ID NO:7, or a guanine at a position corresponding to position 1,841 according to SEQ ID NO:10.

In some embodiments, to determine whether an ERAP1 nucleic acid molecule (genomic nucleic acid molecule, mRNA molecule, or cDNA molecule), or complement thereof, within a biological sample comprises a nucleotide sequence comprising an adenine at a position corresponding to position 21,595 according to SEQ ID NO:3 (genomic nucleic acid molecule), an adenine at a position corresponding to position 1,981 according to SEQ ID NO:8 (mRNA molecule), or an adenine at a position corresponding to position 1,981 according to SEQ ID NO:11 (cDNA molecule), the biological sample can be subjected to an amplification method using a primer pair that includes a first primer derived from the 5' flanking sequence adjacent to an adenine at a position corresponding to position 21,595 according to SEQ ID NO:3, an adenine at a position corresponding to position 1,981 according to SEQ ID NO:8, or an adenine at a position corresponding to position 1,981 according to SEQ ID NO:11, and a second primer derived from the 3' flanking sequence adjacent to an adenine at a position corresponding to position 21,595 according to SEQ ID NO:3, an adenine at a position corresponding to position 1,981 according to SEQ ID NO:8, or an adenine at a position corresponding to position 1,981 according to SEQ ID NO:11 to produce an amplicon that is indicative of the presence of the SNP at positions encoding an adenine at a position corresponding to position 21,595 according to SEQ ID NO:3, an adenine at a position corresponding to position 1,981 according to SEQ ID NO:8, or an adenine at a position corresponding to position 1,981 according to SEQ ID NO:11. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 21,595 according to SEQ ID NO:3, an adenine at a position corresponding to position 1,981 according to SEQ ID NO:8, or an adenine at a position corresponding to position 1,981 according to SEQ ID NO:11, and at least 1, 2, 3, 4, 5, 6, 7, 8, 9, 10, or more nucleotides on each side of positions comprising an adenine at a position corresponding to position 21,595 according to SEQ ID NO:3, an adenine at a position corresponding to position 1,981 according to SEQ ID NO:8, or an adenine at a position corresponding to position 1,981 according to SEQ ID NO:11.

In some embodiments, to determine whether an ERAP1 nucleic acid molecule (genomic nucleic acid molecule, mRNA molecule, or cDNA molecule), or complement thereof, within a biological sample comprises a nucleotide sequence comprising a cytosine at a position corresponding to position 21,811 according to SEQ ID NO:4 (genomic nucleic acid molecule), the biological sample can be subjected to an amplification method using a primer pair that includes a first primer derived from the 5' flanking sequence adjacent to a cytosine at a position corresponding to position 21,811 according to SEQ ID NO:4, and a second primer derived from the 3' flanking sequence adjacent to a cytosine at a position corresponding to position 21,811 according to SEQ ID NO:4 to produce an amplicon that is indicative of the presence of the SNP at positions encoding a cytosine at a position corresponding to position 21,811 according to SEQ ID NO:4. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 21,811 according to SEQ ID NO:4, and at least 1, 2, 3, 4, 5, 6, 7, 8, 9, 10, or more nucleotides on each side of positions comprising a cytosine at a position corresponding to position 21,811 according to SEQ ID NO:4.

In some embodiments, to determine whether an ERAP1 nucleic acid molecule (genomic nucleic acid molecule, mRNA molecule, or cDNA molecule), or complement thereof, within a biological sample comprises a nucleotide sequence comprising a thymine at a position corresponding to position 42,579 according to SEQ ID NO:5 (genomic nucleic acid molecule), the biological sample can be subjected to an amplification method using a primer pair that includes a first primer derived from the 5' flanking sequence adjacent to a thymine at a position corresponding to position 42,579 according to SEQ ID NO:5, and a second primer derived from the 3' flanking sequence adjacent to a thymine at a position corresponding to position 42,579 according to SEQ ID NO:5, to produce an amplicon that is indicative of the presence of the SNP at positions encoding a thymine at a position corresponding to position 42,579 according to SEQ ID NO:5. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 42,579 according to SEQ ID NO:5, and at least 1, 2, 3, 4, 5, 6, 7, 8, 9, 10, or more nucleotides on each side of positions comprising a thymine at a position corresponding to position 42,579 according to SEQ ID NO:5.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of an ERAP1 predicted loss-of-function polypeptide comprising performing an assay on a biological sample obtained from the subject to determine whether an ERAP1 polypeptide in the biological sample contains one or more variations that causes the polypeptide to have a loss-of-function (partial or complete) or predicted loss-of-function (partial or complete). The ERAP1 predicted loss-of-function polypeptide can be any of the ERAP1 predicted loss-of-function polypeptide described herein. In some embodiments, the methods detect the presence of ERAP1 Lys528Arg or Asp575Asn. In some embodiments, the methods detect the presence of ERAP1 Lys528Arg. In some embodiments, the methods detect the presence of ERAP1 Asp575Asn.

In some embodiments, the methods comprise performing an assay on a biological sample obtained from a subject to determine whether an ERAP1 polypeptide in the biological sample comprises: an arginine at a position corresponding to position 528 according to SEQ ID NO:13 or an asparagine at a position corresponding to position 575 according to SEQ ID NO:14.

In some embodiments, the assay comprises sequencing at least a portion of the ERAP1 polypeptide that comprises a position corresponding to: position 528 according to SEQ ID NO:13 or SEQ ID NO:12, or position 575 according to SEQ ID NO:14 or SEQ ID NO:12.

In some embodiments, the assay is an immunoassay for detecting the presence of a ERAP1 polypeptide that comprises a position corresponding to: position 528 according to SEQ ID NO:13 or SEQ ID NO:12, or position 575 according to SEQ ID NO:14 or SEQ ID NO:12.

In some embodiments, when the subject does not have an ERAP1 predicted loss-of-function polypeptide, the subject has an increased risk of developing uveitis. In some embodiments, when the subject has an ERAP1 predicted loss-of-function polypeptide, the subject has a decreased risk of developing uveitis.

The present disclosure also provides isolated nucleic acid molecules that hybridize to ERAP1 variant genomic nucleic acid molecules, ERAP1 variant mRNA molecules, and/or ERAP1 variant cDNA molecules (such as any of the genomic variant nucleic acid molecules, mRNA variant molecules, and cDNA variant molecules disclosed herein). In some embodiments, such isolated nucleic acid molecules hybridize to ERAP1 variant nucleic acid molecules under stringent conditions. Such nucleic acid molecules can be used, for example, as probes, primers, alteration-specific probes, or alteration-specific primers as described or exemplified herein.

In some embodiments, the isolated nucleic acid molecules hybridize to a portion of the ERAP1 nucleic acid molecule that includes a position corresponding to: position 19,474 according to SEQ ID NO:2, position 1,841 according to SEQ ID NO:7, or position 1,841 according to SEQ ID NO:10. In some embodiments, the isolated nucleic acid molecules hybridize to a portion of the ERAP1 nucleic acid molecule that includes a position corresponding to: position 21,595 according to SEQ ID NO:3, position 1,981 according to SEQ ID NO:8, or position 1,981 according to SEQ ID NO:11. In some embodiments, the isolated nucleic acid molecules hybridize to a portion of the ERAP1 nucleic acid molecule that includes a position corresponding: to position 21,811 according to SEQ ID NO:4. In some embodiments, the isolated nucleic acid molecules hybridize to a portion of the ERAP1 nucleic acid molecule that includes a position corresponding to: position 42,579 according to SEQ ID NO:5.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, the isolated alteration-specific probe or alteration-specific primer comprises at least about 15 nucleotides, wherein the alteration-specific probe or alteration-specific primer comprises a nucleotide sequence which is complementary to the nucleotide sequence of a portion of an ERAP1 nucleic acid molecule, or the complement thereof. In some embodiments, the portion comprises a position corresponding to: position 19,474 according to SEQ ID NO:2, or the complement thereof; position 1,841 according to SEQ ID NO:7, or the complement thereof; or position 1,841 according to SEQ ID NO:10, or the complement thereof. In some embodiments, the portion comprises a position corresponding to: position 21,595 according to SEQ ID NO:3, or the complement thereof; position 1,981 according to SEQ ID NO:8, or the complement thereof; or position 1,981 according to SEQ ID NO:11, or the complement thereof. In some embodiments, the portion comprises a position corresponding to: position 21,811 according to SEQ ID NO:4, or the complement thereof. In some embodiments, the portion comprises a position corresponding to: position 42,579 according to SEQ ID NO:5, or the complement thereof.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ERAP1 variant genomic nucleic acid molecules, ERAP1 variant mRNA molecules, and/or ERAP1 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of an ERAP1 variant nucleic acid molecule, wherein the portion comprises a position corresponding to: position 19,474 according to SEQ ID NO:2, or the complement thereof; position 1,841 according to SEQ ID NO:7, or the complement thereof; or position 1,841 according to SEQ ID NO:10, or the complement thereof. In some embodiments, the portion comprises positions corresponding to: positions 19,473-19,475 according to SEQ ID NO:2, or the complement thereof; positions 1,840-1,842 according to SEQ ID NO:7, or the complement thereof; and/or positions 1,840-1,842 according to SEQ ID NO:10, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of an ERAP1 variant nucleic acid molecule, wherein the portion comprises a position corresponding to: position 21,595 according to SEQ ID NO:3, or the complement thereof; position 1,981 according to SEQ ID NO:8, or the complement thereof; or position 1,981 according to SEQ ID NO:11, or the complement thereof. In some embodiments, the portion comprises positions corresponding to: positions 21,595-21,597 according to SEQ ID NO:3, or the complement thereof; positions 1,981-1,983 according to SEQ ID NO:8, or the complement thereof; and/or positions 1,981-1,983 according to SEQ ID NO:11, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of an ERAP1 variant nucleic acid molecule, wherein the portion comprises a position corresponding to: position 21,811 according to SEQ ID NO:4, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of an ERAP1 variant nucleic acid molecule, wherein the portion comprises a position corresponding to: position 42,579 according to SEQ ID NO:5, or the complement thereof.

In some embodiments, the isolated alteration-specific probe or alteration-specific primer comprises at least about 15 nucleotides, wherein the alteration-specific probe or alteration-specific primer comprises a nucleotide sequence which is complementary to the nucleotide sequence of a portion of an ERAP1 nucleic acid molecule, or the complement thereof. In some embodiments, the portion comprises a position corresponding to: position 19,474 according to SEQ ID NO:2, or the complement thereof; position 21,595 according to SEQ ID NO:3, or the complement thereof; position 21,811 according to SEQ ID NO:4, or the complement thereof; position 42,579 according to SEQ ID NO:5, or the complement thereof.

In some embodiments, the portion comprises positions corresponding to: positions 19,473-19,475 according to SEQ ID NO:2, or the complement thereof; positions 21,595-21,597 according to SEQ ID NO:3, or the complement thereof.

In some embodiments, the portion comprises a position corresponding to: position 1,841 according to SEQ ID NO:7, or the complement thereof; or position 1,981 according to SEQ ID NO:8, or the complement thereof.

In some embodiments, the portion comprises positions corresponding to: positions 1,840-1,842 according to SEQ ID NO:7, or the complement thereof; or positions 1,981-1,983 according to SEQ ID NO:8, or the complement thereof.

In some embodiments, the portion comprises a position corresponding to: position 1,841 according to SEQ ID NO:10, or the complement thereof; or position 1,981 according to SEQ ID NO:11, or the complement thereof.

In some embodiments, the portion comprises positions corresponding to: positions 1,840-1,842 according to SEQ ID NO:10, or the complement thereof; or positions 1,981-1,983 according to SEQ ID NO:11, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the ERAP1 variant genomic nucleic acid molecules, ERAP1 variant mRNA molecules, and/or ERAP1 variant cDNA molecules disclosed herein. The primers described herein can be used to amplify the ERAP1 variant genomic nucleic acid molecules, ERAP1 variant mRNA molecules, or ERAP1 variant cDNA molecules, or a fragment thereof.

The present disclosure also provides pairs of primers comprising any of the primers described above. For example, if one of the primers' 3'-ends hybridizes to an adenine at a position corresponding to position 19,474 according to SEQ ID NO:1 (rather than a guanine) in a particular ERAP1 nucleic acid molecule, then the presence of the amplified fragment would indicate the presence of an ERAP1 reference genomic nucleic acid molecule. Conversely, if one of the primers' 3'-ends hybridizes to a guanine at a position corresponding to position 19,474 according to SEQ ID NO:2 (rather than an adenine) in a particular ERAP1 nucleic acid molecule, then the presence of the amplified fragment would indicate the presence of the ERAP1 variant genomic nucleic acid molecule. In some embodiments, the nucleotide of the primer complementary to the guanine at a position corresponding to position 19,474 according to SEQ ID NO:2 can be at the 3' end of the primer. In addition, if one of the primers' 3'-ends hybridizes to an adenine at a position corresponding to position 1,841 according to SEQ IS NO:6 (rather than a guanine) in a particular ERAP1 nucleic acid molecule, then the presence of the amplified fragment would indicate the presence of an ERAP1 reference mRNA molecule. Conversely, if one of the primers' 3'-ends hybridizes to a guanine at a position corresponding to position 1,841 according to SEQ ID NO:7 (rather than an adenine) in a particular ERAP1 mRNA molecule, then the presence of the amplified fragment would indicate the presence of the ERAP1 variant mRNA molecule. In some embodiments, the nucleotide of the primer complementary to the guanine at a position corresponding to position 1,841 according to SEQ ID NO:7 can be at the 3' end of the primer. In addition, if one of the primers' 3'-ends hybridizes to an adenine at a position corresponding to position 1,841 according to SEQ ID NO:9 (rather than a guanine) in a particular ERAP1 nucleic acid molecule, then the presence of the amplified fragment would indicate the presence of an ERAP1 reference cDNA molecule. Conversely, if one of the primers' 3'-ends hybridizes to a guanine at a position corresponding to position 1,841 according to SEQ ID NO:10 (rather than an adenine) in a particular ERAP1 cDNA molecule, then the presence of the amplified fragment would indicate the presence of the ERAP1 variant cDNA molecule. In some embodiments, the nucleotide of the primer complementary to the guanine at a position corresponding to position 1,841 according to SEQ ID NO:10 can be at the 3' end of the primer.

The present disclosure also provides pairs of primers comprising any of the primers described above. For example, if one of the primers' 3'-ends hybridizes to a guanine at a position corresponding to position 21,595 according to SEQ ID NO:1 (rather than an adenine) in a particular ERAP1 nucleic acid molecule, then the presence of the amplified fragment would indicate the presence of an ERAP1 reference genomic nucleic acid molecule. Conversely, if one of the primers' 3'-ends hybridizes to an adenine at a position corresponding to position 21,595 according to SEQ ID NO:3 (rather than a guanine) in a particular ERAP1 nucleic acid molecule, then the presence of the amplified fragment would indicate the presence of the ERAP1 variant genomic nucleic acid molecule. In some embodiments, the nucleotide of the primer complementary to the adenine at a position corresponding to position 21,595 according to SEQ ID NO:3 can be at the 3' end of the primer. In addition, if one of the primers' 3'-ends hybridizes to a guanine at a position corresponding to position 1,981 according to SEQ IS NO:6 (rather than an adenine) in a particular ERAP1 nucleic acid molecule, then the presence of the amplified fragment would indicate the presence of an ERAP1 reference mRNA molecule. Conversely, if one of the primers' 3'-ends hybridizes to an adenine at a position corresponding to position 1,981 according to SEQ ID NO:8 (rather than a guanine) in a particular ERAP1 mRNA molecule, then the presence of the amplified fragment would indicate the presence of the ERAP1 variant mRNA molecule. In some embodiments, the nucleotide of the primer complementary to the adenine at a position corresponding to position 1,981 according to SEQ ID NO:8 can be at the 3' end of the primer. In addition, if one of the primers' 3'-ends hybridizes to a guanine at a position corresponding to position 1,981 according to SEQ ID NO:9 (rather than an adenine) in a particular ERAP1 nucleic acid molecule, then the presence of the amplified fragment would indicate the presence of an ERAP1 reference cDNA molecule. Conversely, if one of the primers' 3'-ends hybridizes to an adenine at a position corresponding to position 1,981 according to SEQ ID NO:11 (rather than a guanine) in a particular ERAP1 cDNA molecule, then the presence of the amplified fragment would indicate the presence of the ERAP1 variant cDNA molecule. In some embodiments, the nucleotide of the primer complementary to the adenine at a position corresponding to position 1,981 according to SEQ ID NO:11 can be at the 3' end of the primer.

The present disclosure also provides pairs of primers comprising any of the primers described above. For example, if one of the primers' 3'-ends hybridizes to a thymine at a position corresponding to position 21,811 according to SEQ ID NO:1 (rather than a cytosine) in a particular ERAP1 nucleic acid molecule, then the presence of the amplified fragment would indicate the presence of an ERAP1 reference genomic nucleic acid molecule. Conversely, if one of the primers' 3'-ends hybridizes to a cytosine at a position corresponding to position 21,811 according to SEQ ID NO:4 (rather than a thymine) in a particular ERAP1 nucleic acid molecule, then the presence of the amplified fragment would indicate the presence of the ERAP1 variant genomic nucleic acid molecule. In some embodiments, the nucleotide of the primer complementary to the cytosine at a position corresponding to position 21,811 according to SEQ ID NO:4 can be at the 3' end of the primer.

The present disclosure also provides pairs of primers comprising any of the primers described above. For example, if one of the primers' 3'-ends hybridizes to a cytosine at a position corresponding to position 42,579 according to SEQ ID NO:1 (rather than a thymine) in a particular ERAP1 nucleic acid molecule, then the presence of the amplified fragment would indicate the presence of an ERAP1 reference genomic nucleic acid molecule. Conversely, if one of the primers' 3'-ends hybridizes to a thymine at a position corresponding to position 42,579 according to SEQ ID NO:5 (rather than a cytosine) in a particular ERAP1 nucleic acid molecule, then the presence of the amplified fragment would indicate the presence of the ERAP1 variant genomic nucleic acid molecule. In some embodiments, the nucleotide of the primer complementary to the thymine at a position corresponding to position 42,579 according to SEQ ID NO:5 can be at the 3' end of the primer.

In the context of the present disclosure "specifically hybridizes" means that the probe or primer (such as, for example, the alteration-specific probe or alteration-specific primer) does not hybridize to a nucleotide sequence encoding an ERAP1 reference genomic nucleic acid molecule, an ERAP1 reference mRNA molecule, and/or an ERAP1 reference cDNA molecule.

In any of the embodiments described throughout the present disclosure, the probes (such as, for example, an alteration-specific probe) can comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well. In some embodiments, the support is a microarray.

The present disclosure also provides molecular complexes comprising or consisting of any of the ERAP1 nucleic acid molecules (genomic nucleic acid molecules, mRNA molecules, or cDNA molecules), or complement thereof, described herein and any of the alteration-specific primers or alteration-specific probes described herein. In some embodiments, the ERAP1 nucleic acid molecules (genomic nucleic acid molecules, mRNA molecules, or cDNA molecules), or complement thereof, in the molecular complexes are single-stranded. In some embodiments, the ERAP1 nucleic acid molecule is any of the genomic nucleic acid molecules described herein. In some embodiments, the ERAP1 nucleic acid molecule is any of the mRNA molecules described herein. In some embodiments, the ERAP1 nucleic acid molecule is any of the cDNA molecules described herein. In some embodiments, the molecular complex comprises or consists of any of the ERAP1 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the ERAP1 nucleic acid molecules (genomic nucleic acid molecules, mRNA molecules, or cDNA molecules), or complement thereof, described herein and any of the alteration-specific probes described herein.

In some embodiments, the molecular complex comprises an alteration-specific primer or an alteration-specific probe hybridized to an ERAP1 genomic nucleic acid molecule, wherein the alteration-specific primer or the alteration-specific probe is hybridized to the ERAP1 genomic nucleic acid molecule at a position corresponding to: position 19,474 according to SEQ ID NO:2, or the complement thereof; position 21,595 according to SEQ ID NO:3, or the complement thereof; position 21,811 according to SEQ ID NO:4, or the complement thereof; or position 42,579 according to SEQ ID NO:5, or the complement thereof.

In some embodiments, the alteration-specific primer or the alteration-specific probe in the molecular complex is hybridized to: an AGG codon at positions corresponding to positions 19,473-19,475 according to SEQ ID NO:2 or an AAC codon at positions corresponding to positions 21,595-21,597 according to SEQ ID NO:3.

In some embodiments, the genomic nucleic acid molecule in the molecular complex comprises SEQ ID NO:2, SEQ ID NO:3, SEQ ID NO:4, or SEQ ID NO:5.

In some embodiments, the molecular complex comprises an alteration-specific primer or an alteration-specific probe hybridized to an ERAP1 mRNA molecule, wherein the alteration-specific primer or the alteration-specific probe is hybridized to the ERAP1 mRNA molecule at a position corresponding to: position 1,841 according to SEQ ID NO:7, or the complement thereof; or position 1,981 according to SEQ ID NO:8, or the complement thereof.

In some embodiments, the alteration-specific primer or the alteration-specific probe in the molecular complex is hybridized to: an AGG codon at positions corresponding to positions 1,840-1,842 according to SEQ ID NO:7 or an AAC codon at positions corresponding to positions 1,981-1,983 according to SEQ ID NO:8.

In some embodiments, the mRNA molecule in the molecular complex comprises SEQ ID NO:7 or SEQ ID NO:8.

In some embodiments, the molecular complex comprises an alteration-specific primer or an alteration-specific probe hybridized to an ERAP1 cDNA molecule, wherein the alteration-specific primer or the alteration-specific probe is hybridized to the ERAP1 cDNA molecule at a position corresponding to: position 1,841 according to SEQ ID NO:10, or the complement thereof; or position 1,981 according to SEQ ID NO:11, or the complement thereof.

In some embodiments, the alteration-specific primer or the alteration-specific probe in the molecular complex is hybridized to: an AGG codon at positions corresponding to positions 1,840-1,842 according to SEQ ID NO:10 or an AAC codon at positions corresponding to positions 1,981-1,983 according to SEQ ID NO:1.

In some embodiments, the cDNA molecule in the molecular complex comprises SEQ ID NO:10, SEQ ID NO:11.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The nucleotide sequence of an ERAP1 reference genomic nucleic acid molecule is set forth in SEQ ID NO:1. Referring to SEQ ID NO:1, position 19,474 is an adenine. Referring to SEQ ID NO:1, position 21,595 is a guanine. Referring to SEQ ID NO:1, position 21,811 is a thymine. Referring to SEQ ID NO:1, position 42,579 is a cytosine.

An ERAP1 variant genomic nucleic acid molecule exists, wherein the adenine at position 19,474 is replaced with a guanine. The nucleotide sequence of this ERAP1 variant genomic nucleic acid molecule is set forth in SEQ ID NO:2.

Another ERAP1 variant genomic nucleic acid molecule exists, wherein the guanine at position 21,595 is replaced with an adenine. The nucleotide sequence of this ERAP1 variant genomic nucleic acid molecule is set forth in SEQ ID NO:3.

Another ERAP1 variant genomic nucleic acid molecule exists, wherein the thymine at position 21,811 is replaced with a cytosine. The nucleotide sequence of this ERAP1 variant genomic nucleic acid molecule is set forth in SEQ ID NO:4.

Another ERAP1 variant genomic nucleic acid molecule exists, wherein the cytosine at position 42,579 is replaced with a thymine. The nucleotide sequence of this ERAP1 variant genomic nucleic acid molecule is set forth in SEQ ID NO:5.

The nucleotide sequence of an ERAP1 reference mRNA molecule is set forth in SEQ ID NO:6. Referring to SEQ IS NO:6, position 1,841 is an adenine. Referring to SEQ ID NO:6, position 1,981 is a guanine.

An ERAP1 variant mRNA molecule exists, wherein the adenine at position 1,841 is replaced with a guanine. The nucleotide sequence of this ERAP1 variant mRNA molecule is set forth in SEQ ID NO:7.

Another ERAP1 variant mRNA molecule exists, wherein the guanine at position 1,981 is replaced with an adenine. The nucleotide sequence of this ERAP1 variant mRNA molecule is set forth in SEQ ID NO:8.

The nucleotide sequence of an ERAP1 reference cDNA molecule is set forth in SEQ ID NO:9. Referring to SEQ ID NO:9, position 1,841 is an adenine. Referring to SEQ ID NO:9, position 1,981 is a guanine.

An ERAP1 variant cDNA molecule exists, wherein the adenine at position 1,841 is replaced with a guanine. The nucleotide sequence of this ERAP1 variant cDNA molecule is set forth in SEQ ID NO:10.

Another ERAP1 variant cDNA molecule exists, wherein the guanine at position 1,981 is replaced with an adenine. The nucleotide sequence of this ERAP1 variant cDNA molecule is set forth in SEQ ID NO:11.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ IS NO:6, or SEQ ID NO:9). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, an ERAP1 nucleic acid molecule comprising a nucleotide sequence that comprises a guanine at a position corresponding to position 19,474 according to SEQ ID NO:2 means that if the nucleotide sequence of the ERAP1 genomic nucleic acid molecule is aligned to the sequence of SEQ ID NO:2, the ERAP1 sequence has a guanine residue at the position that corresponds to position 19,474 of SEQ ID NO:2. The same applies for ERAP1 mRNA molecules comprising a nucleotide sequence that comprises a guanine at a position corresponding to position 1,841 according to SEQ ID NO:7, and ERAP1 cDNA molecules comprising a nucleotide sequence that comprises a guanine at a position corresponding to position 1,841 according to SEQ ID NO:10). These phrases refer to an ERAP1 nucleic acid molecule, wherein the genomic nucleic acid molecule has a nucleotide sequence that comprises a guanine residue that is homologous to the guanine residue at position 19,474 of SEQ ID NO:2 (or wherein the mRNA molecule has a nucleotide sequence that comprises a guanine residue that is homologous to the guanine residue at position 1,841 of SEQ ID NO:7, or wherein the cDNA molecule has a nucleotide sequence that comprises a guanine residue that is homologous to the guanine residue at position 1,841 of SEQ ID NO:10).

As described herein, a position within an ERAP1 genomic nucleic acid molecule that corresponds to position 19,474 according to SEQ ID NO:2, for example, can be identified by performing a sequence alignment between the nucleotide sequence of a particular ERAP1 nucleic acid molecule and the nucleotide sequence of SEQ ID NO:2. A variety of computational algorithms exist that can be used for performing a sequence alignment to identify a nucleotide position that corresponds to, for example, position 19,474 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of an ERAP1 reference polypeptide is set forth in SEQ ID NO:12. Referring to SEQ ID NO:12, the ERAP1 reference polypeptide is 948 amino acids in length. Referring to SEQ ID NO:12, position 528 is a lysine. Referring to SEQ ID NO:12, position 575 is an aspartic acid.

An ERAP1 predicted loss-of-function polypeptide exists (Lys528Arg), the amino acid sequence of which is set forth in SEQ ID NO:13. Referring to SEQ ID NO:13, the ERAP1 predicted loss-of-function polypeptide is 948 amino acids in length. Referring to SEQ ID NO:13, position 528 is an arginine.

Another ERAP1 predicted loss-of-function polypeptide exists (Asp575Asn), the amino acid sequence of which is set forth in SEQ ID NO:14. Referring to SEQ ID NO:14, the ERAP1 predicted loss-of-function polypeptide is 948 amino acids in length. Referring to SEQ ID NO:14, position 575 is an asparagine.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit uveitis, such as anterior uveitis, for use in the treatment of uveitis (or for use in the preparation of a medicament for treating uveitis) in a subject, wherein the subject has any of the ERAP1 variant genomic nucleic acid molecules, variant mRNA molecules, and/or variant cDNA molecules described herein. The therapeutic agents that treat or inhibit uveitis can be any of the therapeutic agents that treat or inhibit uveitis described herein.

In some embodiments, the subject is identified as having an ERAP1 variant genomic nucleic acid molecule, or the complement thereof, wherein the genomic nucleic acid molecule has a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof.

In some embodiments, the subject is identified as having an ERAP1 variant mRNA molecule, or the complement thereof, wherein the mRNA molecule has a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof.

In some embodiments, the subject is identified as having an ERAP1 variant cDNA molecule, or the complement thereof, wherein the cDNA molecule has a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

In some embodiments, the subject is identified as having: a genomic nucleic acid molecule having a nucleotide sequence that comprises a guanine at a position corresponding to position 19,474 according to SEQ ID NO:2, or the complement thereof; an mRNA molecule having a nucleotide sequence that comprises a guanine at a position corresponding to position 1,841 according to SEQ ID NO:7, or the complement thereof; a cDNA molecule having a nucleotide sequence that comprises a guanine at a position corresponding to position 1,841 according to SEQ ID NO:10, or the complement thereof; or an ERAP1 predicted loss-of-function polypeptide that comprises an arginine at a position corresponding to position 528 according to SEQ ID NO:13.

In some embodiments, the subject is identified as having: a genomic nucleic acid molecule having a nucleotide sequence that comprises an adenine at a position corresponding to position 21,595 according to SEQ ID NO:3, or the complement thereof; an mRNA molecule having a nucleotide sequence that comprises an adenine at a position corresponding to position 1,981 according to SEQ ID NO:8, or the complement thereof; a cDNA molecule having a nucleotide sequence that comprises an adenine at a position corresponding to position 1,981 according to SEQ ID NO:11, or the complement thereof; or an ERAP1 predicted loss-of-function polypeptide that comprises an asparagine at a position corresponding to position 575 according to SEQ ID NO:14.

In some embodiments, the subject is identified as having: a genomic nucleic acid molecule having a nucleotide sequence that comprises a cytosine at a position corresponding to position 21,811 according to SEQ ID NO:4, or the complement thereof.

In some embodiments, the subject is identified as having: a genomic nucleic acid molecule having a nucleotide sequence that comprises a thymine at a position corresponding to position 42,579 according to SEQ ID NO:5, or the complement thereof.

The present disclosure also provides ERAP1 inhibitors for use in the treatment of uveitis, such as anterior uveitis (or for use in the preparation of a medicament for treating uveitis) in a subject, wherein the subject is heterozygous for any of the ERAP1 variant genomic nucleic acid molecules, variant mRNA molecules, and/or variant cDNA molecules described herein, or wherein the subject is reference for an ERAP1 genomic nucleic acid molecule, mRNA molecule, or cDNA molecule.

In some embodiments, the subject is reference for an ERAP1 genomic nucleic acid molecule, an ERAP1 mRNA molecule, or an ERAP1 cDNA molecule.

In some embodiments, the subject is heterozygous for a genomic nucleic acid molecule, or the complement thereof, wherein the genomic nucleic acid molecule has a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof.

In some embodiments, the subject is heterozygous for an mRNA molecule, or the complement thereof, wherein the mRNA molecule has a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof.

In some embodiments, the subject is heterozygous for a cDNA molecule, or the complement thereof, wherein the cDNA molecule has a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

In some embodiments, the subject is identified as being heterozygous for: a genomic nucleic acid molecule having a nucleotide sequence that comprises a guanine at a position corresponding to position 19,474 according to SEQ ID NO:2, or the complement thereof; an mRNA molecule having a nucleotide sequence that comprises a guanine at a position corresponding to position 1,841 according to SEQ ID NO:7, or the complement thereof; a cDNA molecule having a nucleotide sequence that comprises a guanine at a position corresponding to position 1,841 according to SEQ ID NO:10, or the complement thereof; or an ERAP1 predicted loss-of-function polypeptide that comprises an arginine at a position corresponding to position 528 according to SEQ ID NO:13. The ERAP1 inhibitors can be any of the ERAP1 inhibitors described herein.

In some embodiments, the subject is identified as being heterozygous for: a genomic nucleic acid molecule having a nucleotide sequence that comprises an adenine at a position corresponding to position 21,595 according to SEQ ID NO:3, or the complement thereof; an mRNA molecule having a nucleotide sequence that comprises an adenine at a position corresponding to position 1,981 according to SEQ ID NO:8, or the complement thereof; a cDNA molecule having a nucleotide sequence that comprises an adenine at a position corresponding to position 1,981 according to SEQ ID NO:11, or the complement thereof; or an ERAP1 predicted loss-of-function polypeptide that comprises an asparagine at a position corresponding to position 575 according to SEQ ID NO:14. The ERAP1 inhibitors can be any of the ERAP1 inhibitors described herein.

In some embodiments, the subject is identified as being heterozygous for: a genomic nucleic acid molecule having a nucleotide sequence that comprises a cytosine at a position corresponding to position 21,811 according to SEQ ID NO:4, or the complement thereof. The ERAP1 inhibitors can be any of the ERAP1 inhibitors described herein.

In some embodiments, the subject is identified as being heterozygous for: a genomic nucleic acid molecule having a nucleotide sequence that comprises a thymine at a position corresponding to position 42,579 according to SEQ ID NO:5, or the complement thereof. The ERAP1 inhibitors can be any of the ERAP1 inhibitors described herein.

In some embodiments, the subject is identified as having: an ERAP1 reference genomic nucleic acid molecule comprising SEQ ID NO:1, an ERAP1 reference mRNA molecule comprising SEQ IS NO:6, an ERAP1 reference cDNA molecule comprising SEQ ID NO:9, or an ERAP1 reference polypeptide comprising SEQ ID NO:12. The ERAP1 inhibitors can be any of the ERAP1 inhibitors described herein.

The present disclosure also provides a combination of one or more ERAP1 inhibitors and one or more HLA-B27 inhibitors for use in the treatment of uveitis, such as anterior uveitis (or for use in the preparation of a medicament for treating uveitis) in a subject, wherein the subject is heterozygous for any of the ERAP1 variant genomic nucleic acid molecules, variant mRNA molecules, and/or variant cDNA molecules described herein, or wherein the subject is reference for an ERAP1 genomic nucleic acid molecule, mRNA molecule, or cDNA molecule.

In some embodiments, the subject is reference for an ERAP1 genomic nucleic acid molecule, an ERAP1 mRNA molecule, or an ERAP1 cDNA molecule.

In some embodiments, the subject is heterozygous for a genomic nucleic acid molecule, or the complement thereof, wherein the genomic nucleic acid molecule has a nucleotide sequence comprising: a guanine at a position corresponding to position 19,474 according to SEQ ID NO:2, or the complement thereof; an adenine at a position corresponding to position 21,595 according to SEQ ID NO:3, or the complement thereof; a cytosine at a position corresponding to position 21,811 according to SEQ ID NO:4, or the complement thereof; or a thymine at a position corresponding to position 42,579 according to SEQ ID NO:5, or the complement thereof.

In some embodiments, the subject is heterozygous for an mRNA molecule, or the complement thereof, wherein the mRNA molecule has a nucleotide sequence comprising: a guanine at a position corresponding to position 1,841 according to SEQ ID NO:7, or the complement thereof; or an adenine at a position corresponding to position 1,981 according to SEQ ID NO:8, or the complement thereof.

In some embodiments, the subject is heterozygous for a cDNA molecule, or the complement thereof, wherein the cDNA molecule has a nucleotide sequence comprising: a guanine at a position corresponding to position 1,841 according to SEQ ID NO:10, or the complement thereof; or an adenine at a position corresponding to position 1,981 according to SEQ ID NO:11, or the complement thereof.

In some embodiments, the subject is identified as being heterozygous for: a genomic nucleic acid molecule having a nucleotide sequence that comprises a guanine at a position corresponding to position 19,474 according to SEQ ID NO:2, or the complement thereof; an mRNA molecule having a nucleotide sequence that comprises a guanine at a position corresponding to position 1,841 according to SEQ ID NO:7, or the complement thereof; a cDNA molecule having a nucleotide sequence that comprises a guanine at a position corresponding to position 1,841 according to SEQ ID NO:10, or the complement thereof; or an ERAP1 predicted loss-of-function polypeptide that comprises an arginine at a position corresponding to position 528 according to SEQ ID NO:13. The ERAP1 inhibitors can be any of the ERAP1 inhibitors described herein.

In some embodiments, the subject is identified as being heterozygous for: a genomic nucleic acid molecule having a nucleotide sequence that comprises an adenine at a position corresponding to position 21,595 according to SEQ ID NO:3, or the complement thereof; an mRNA molecule having a nucleotide sequence that comprises an adenine at a position corresponding to position 1,981 according to SEQ ID NO:8, or the complement thereof; a cDNA molecule having a nucleotide sequence that comprises an adenine at a position corresponding to position 1,981 according to SEQ ID NO:11, or the complement thereof; or an ERAP1 predicted loss-of-function polypeptide that comprises an asparagine at a position corresponding to position 575 according to SEQ ID NO:14. The ERAP1 inhibitors can be any of the ERAP1 inhibitors described herein.

In some embodiments, the subject is identified as being heterozygous for: a genomic nucleic acid molecule having a nucleotide sequence that comprises a cytosine at a position corresponding to position 21,811 according to SEQ ID NO:4, or the complement thereof. The ERAP1 inhibitors can be any of the ERAP1 inhibitors described herein.

In some embodiments, the subject is identified as being heterozygous for: a genomic nucleic acid molecule having a nucleotide sequence that comprises a thymine at a position corresponding to position 42,579 according to SEQ ID NO:5, or the complement thereof. The ERAP1 inhibitors can be any of the ERAP1 inhibitors described herein.

In some embodiments, the subject is identified as having: an ERAP1 reference genomic nucleic acid molecule comprising SEQ ID NO:1, an ERAP1 reference mRNA molecule comprising SEQ IS NO:6, an ERAP1 reference cDNA molecule comprising SEQ ID NO:9, or an ERAP1 reference polypeptide comprising SEQ ID NO:12. The ERAP1 inhibitors can be any of the ERAP1 inhibitors described herein.

The present disclosure also provides pharmaceutical compositions comprising one or more ERAP1 inhibitors in combination with one or more HLA-B27 inhibitors.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: General Methodology

Sequencing and Genotyping

Genotyping and exome sequencing were performed as previously described (Verweij et al., N. Engl. J. Med., 2022, 387, 332-344). In short, for analyses of common variants, array genotyping data was used and imputation was performed with the use of the TOPMed panel (Taliun et al., Nature, 2021, 590, 290-299) in all cohorts analyzed. Exome sequencing for rare variant analysis was performed with the use of Illumina HiSeq 2500-v4 or Illumina NovaSeq instruments, with 75-bp paired-end reads (Taliun et al., Nature, 2021, 590, 290-299). Deleterious variants were considered if annotated as: frameshift, stop-gain, stop-loss, splice acceptor, splice donor, in-frame insertion or deletion (indel), missense, and other annotations. Frameshift, stop-gain, stop-loss, splice-acceptor, and splice-donor alleles were categorized as predicted loss-of-function variants. The alternative-allele frequency and functional annotation of each variant were used to generate seven genotypes based on the combined variant burden: predicted loss-of-function variants with an alternative-allele frequency thresholds of 1% and 0.1%, predicted loss-of-function variants plus missense variants that were predicted to be deleterious and had an alternative-allele frequency thresholds of 1% and 0.1%.

Samples

Genome-wide association analyses were performed in the U. K. Biobank population-based cohort, and in the Geisinger Health System MyCode cohort. Others datasets: 29,237 from the Malmo Diet and Cancer Study, 41,400 participants from the University of Pennsylvania Penn Medicine BioBank, 29,845 participants from the Mount Sinai BioMe BioBank, 49,004 from the Colorado cohort, 40,197 from the UCLA cohort, and 115,418 participants MAYO-clinic cohort.

Exome Sequencing and Whole-Genome Genotyping

For analyses of common variants, array genotyping data was used and imputation was performed with the use of the TOPMed reference panel (Taliun et al., bioRxiv, 563866, doi:10.1101/563866, 2019; and Das et al., Nat. Genet., 2016, 48, 1284-1287). High-coverage exome sequencing was performed with the use of Illumina HiSeq 2500-v4 or Illumina NovaSeq instruments, with 75-bp paired-end reads. The GRCh38 human genome reference sequence and Ensembl, version 85, gene definitions were used for variant identification and annotation. Variants were classified from most to least deleterious in the following order: frameshift, stop-gain, stop-loss, splice acceptor, splice donor, in-frame insertion or deletion (indel), missense, and other annotations. Frameshift, stop-gain, stop-loss, splice-acceptor, and splice-donor alleles were categorized as predicted loss-of-function variants. Missense variants were classified using computer modeling to predict functional effects with five algorithms: SIFT, Polyphen-2 HDIV, Polyphen-2 HVAR, LRT, and MutationTaster. To account for the fact that different genes have different types and frequencies of potentially causative variants, the alternative-allele frequency and functional annotation of each variant was used to generate seven genotypes based on the combined variant burden: predicted loss-of-function variants with an alternative-allele frequency of less than 1%, predicted loss-of-function variants plus missense variants that were predicted to be deleterious by five of five algorithms and had an alternative-allele frequency of less than 1% or less than 0.1%, predicted loss-of-function variants plus missense variants that were predicted to be deleterious by at least one of five algorithms and had an alternative-allele frequency of less than 1% or less than 0.1%, and predicted loss-of-function variants plus any missense variants with an alternative-allele frequency of less than 1% or less than 0.1%.

Statistical Analysis

Associations between genotypes and phenotypes was estimated by fitting linear regression models (for quantitative traits) or Firth bias-corrected logistic regression models (for binary traits) using REGENIE software, version 2+. Analyses were stratified according to cohort and ancestry and were adjusted for age, age squared, sex, age-by-sex, and age squared-by-sex interaction terms; experimental batch-related covariates; the first 10 common variant-derived genetic principal components; the first 20 rare variant-derived principal components; and a polygenic score generated by REGENIE, which robustly adjusts for relatedness and population structure. A meta-analysis of association results across cohorts and ancestries was performed with a fixed-effect inverse-variance-weighted approach. For other analyses, a two-tailed P value of 0.05 was used.

Example 2: Decreased Expression of ERAP1 is Protective for B27-Anterior Uveitis

For the largest AU case cohort to date, eight large EHR based populations, reaching 3,850 AU cases and 916,325 controls (Table 2) were sequenced.

TABLE 2

Overview of studies included in the meta-analysis

| Cohort | EUR | | ALL | |
| --- | --- | --- | --- | --- |
| | Cases (% B27) | Ctrls (% B27) | Cases (% B27) | Ctrls (% B27) |
| UKB450k | 1,260 ( ) | 429,728 ( ) | 1,388 ( ) | 452,976 ( ) |
| GHS175K | 1,007 | 150,547 | 1,066 | 159,644 |
| UPenn-PMBB | 75 | 28,426 | 233 | 41,167 |
| Sinai | 51 | 10,681 | 169 | 29,676 |
| MALMO | 114 | 28,834 | 116 | 29,121 |
| MAYO-Clinic | 331 | 110,930 | 355 | 115,063 |
| UCLA | 161 | 26,276 | 305 | 39,892 |
| Colorado | 181 | 40,980 | 218 | 48,786 |
| Total | 3,180 | 826,402 | 3,850 | 916,325 |

Examining the association of common variants, two genome wide significant signals were discovered: a risk signal for rs543685299 at the HLA-B locus (OR(95% CI)=3.37 (3.12-3.65), p=7.82E-197) and a signal for rs3198304 at the ERAP1 locus (OR(95% CI)=0.84 (0.79-0.89), p=5.02e-9) that presents protection from AU (data not shown). The top ERAP1 SNP shows a replicated direction of protection in 6/8 cohorts (FIG. 1) and is found significantly protective in the two larger cohorts of UKB and GHS.

The analysis was repeated using an EUR-only cohort of 3,180 EUR cases and 826,348 controls. In this less powered analysis, 17% of total cases and 10% of controls were removed, yet similar signals were found for both HLA-B (OR=3.4, p=9.7e-186) and ERAP1 (OR=0.83, p=3.2e-09).

ERAP1 is an ER-Aminopeptidase that trims peptides to be loaded and presented by MHC class-I proteins. Therefore, regulating the expression of ERAP1 will change the peptidome that is available for presentation by HLA Class-I alleles; in this case, by HLA-B27. This will have a direct effect on what antigens are presented by HLA-B27, and the subsequent activation of the immune response in AU.

Aside from the two significant common loci, no rare variants with allele frequency (AF) less than 0.5% showed genome wide significance. Similarly, several gene-burden analyses with various AF thresholds were examined and discovered no significant gene-burden results.

Example 3: ERAP1 Signal is Strengthened and is the Only Genome Wide Significant Signal in the Analysis of B27 Carriers The above results show that the strongest genetic risk for AU is attributed to HLA-B, a known signal attributable to the HLA-B27 allele (Linssen et al., Invest. Ophthalmol. Vis. Sci., 1991, 32, 2568-2578; and Sheehan, J. R. Soc. Med., 2004, 97, 10-14). This risk was observed to be different within each cohort, that ranges between OR=2.4 in the GHS cohort to OR=4.3 in the UKB cohort. To correct for this difference between the cohort, and to examine the genetic signals that underly the HLA-B27 association, the cohorts were stratified by the carrier status of HLA-B27 using the HLA-B27 tag SNP rs4349859. The HLA-B27 stratification resulted in two cohorts: 1) a B27-positive cohort with samples carrying either one or two copies of the tag SNP, and 2) a B27-negative cohort with samples carrying zero copies of the tag SNP. The B27-positive cohort consisted of 856 AU cases and 70,198 controls, suggesting that 22.23% of the AU cases carry the B27 allele, a significant enrichment than the controls, where 7.7% are B27 carriers, as expected from general population B27 frequency. The final analysis of all ancestries included 837 B27-positive AU cases and 67,755 B27-positive controls, a meta-analysis including seven main cohorts, and excluding the UPENN cohort that was underpowered for a valid analysis with 19 cases and 2,434 controls.

The HLA-B signal was completely diminished in a B27-stratified analysis, while the ERAP1 signal remained the only genome wide significant locus. Moreover, the protective effect observed was stronger when examining the small B27-stratified cohort (rs27529, OR=0.74, p=1.3e-9), even though this cohort is much less powered with only 22% of cases and 7.7% of the controls (data not shown). Furthermore, the top ERAP1 variant was part of a significant haplotype that included ERAP1 missense variant K528R-rs30187 (R2=1, D'=1). This haplotype has been shown to be an eQTL that significantly decreases ERAP1 expression and is associated with other HLA class-I related disorders such as Ankylosing Spondylitis and Psoriatic Arthritis (data not shown).

The above analysis was repeated with a EUR-only cohort, consisting of 795 AU cases and 65,628 controls. Of note, the proportion of B27-positive AU cases was higher in EUR than in the full all-ancestries analysis, reaching 25% of cases, which is still much lower than the ~50% B27-AU carriers previously reported. The proportion of B27 carriers in controls remained 8% as expected for EUR population.

Figure 2:
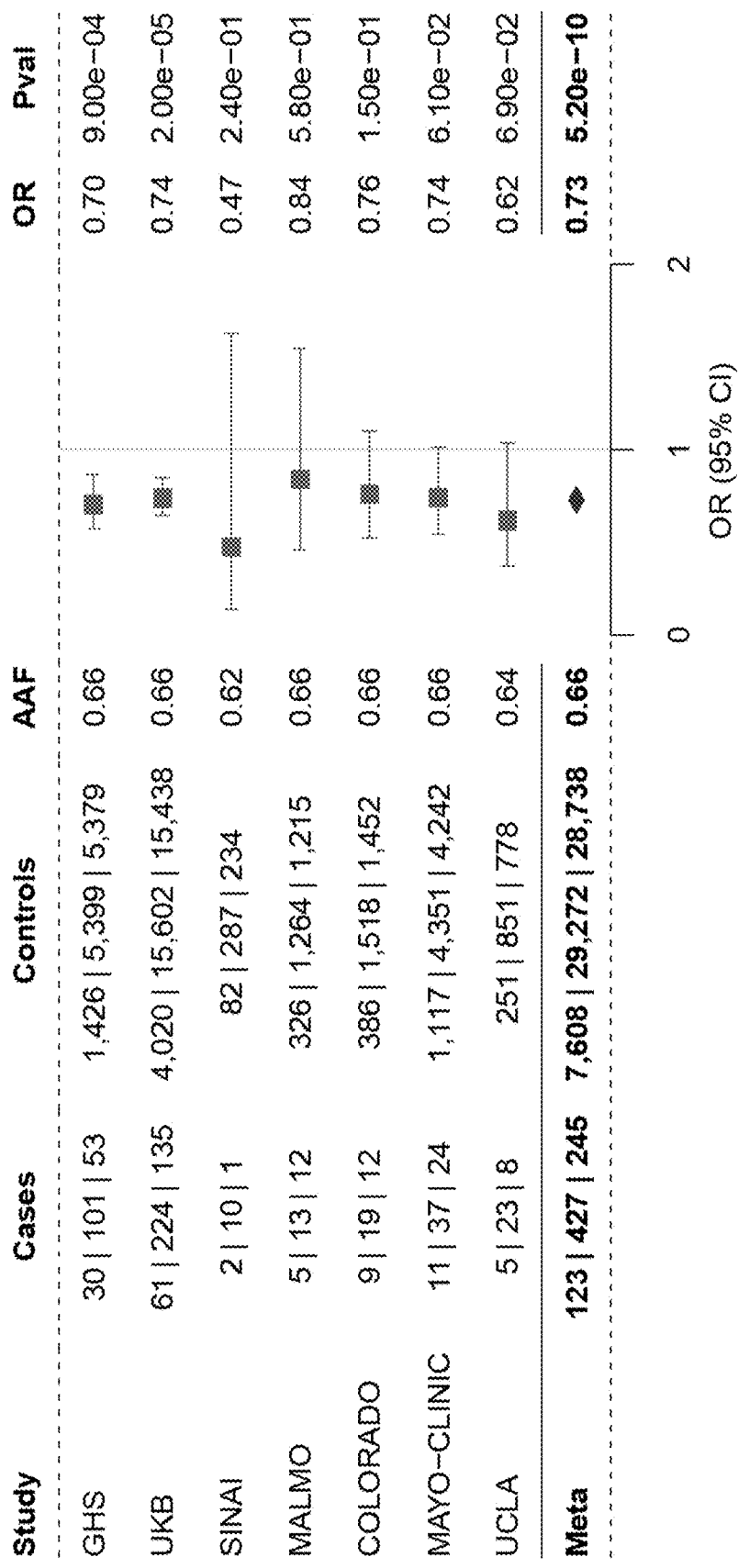
FIG. 2 shows ERAP1 protection across seven B27-positive cohorts.

The EUR-only, B27-positive analysis did also present with more significant results for the protective ERAP1 locus, exhibiting a slightly better OR (95% CI)=0.73 (1.78-3.76), and a stronger p=5.2e-10 (FIG. 2). When examining the effect of the ERAP1 haplotype across the seven remaining B27-positive cohorts, the protective effect of the common ERAP1 haplotype was evident in all cohorts, ranging from OR=0.47 in the small Sinai cohort, to OR=0.84 in the MALMO cohort. This analysis was very much underpowered considering the exclusion of most cases and controls, resulting in a nominal p-value in the two larger cohorts of GHS (184 cases) and UKB (420 cases).

AU is a symptom commonly observed in other class-I-opathies such as AS (~50%). Furthermore, a significant ERAP1 signal was observed previously for AS, which is also a B27-associated disease. Psoriatic Arthritis is another MHC-class-I disease that has similar associations with ERAP1 and AU. A strict analysis was therefore designed, removing all samples diagnosed with either AS (ICD10-M45) or Ps (ICD10-L40) from an already underpowered B27-positive cohort. When considering only B27 carriers that were not diagnosed with either AS or Ps, 618 AU cases and 67,343 controls in all eight cohorts including all ancestries were identified. This sets the proportion of AU cases that are diagnosed also with AS or Ps at 28%. Within the general B27 controls, 4% were found to have AS or Ps diagnosis.

In the final analysis of AU without AS or Ps, six cohorts that were sufficiently powered were combined and considered 605 AU cases and 64,991 controls of all ancestries. In this analysis, ERAP1 locus presented a similar protection of OR=0.75, with slightly lower p=8.2e-6. In a EUR-only analysis consisting of 569 EUR AU cases and 62,360 controls, a similar signal (OR=0.74 and p=9.6e-6) was observed.

Figure 3:
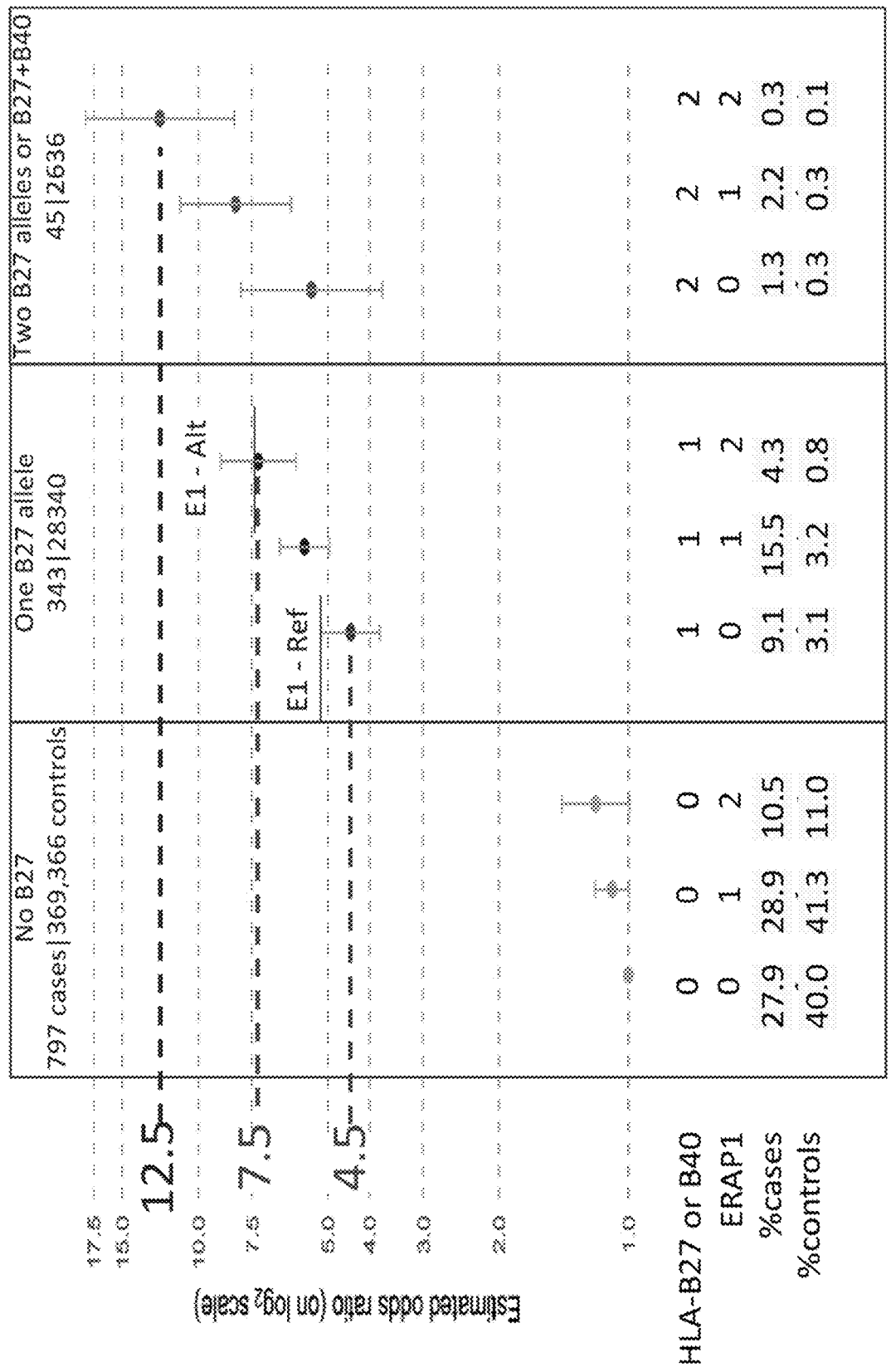
FIG. 3 shows the combined risk for anterior uveitis with ERAP1 and HLA-B27/HLA-B40.

An Additive Effect for 827-AU Risk with the Combined Effect of Having Two Copies of HLA Risk Alleles and the ERAP1 Risk Haplotypes The effect of the ERAP1 risk haplotype (tagged by r530187) was protective in subjects carrying at least one copy of the HLA-B27 allele, with a further increase in subjects carrying a second HLA-B27 allele or the HLA-B40 risk allele (FIG. 3). The risk was assessed in AU samples from the GHS+UKB cohorts combined, where HLA typing was done by imputation for increased accuracy (vs. tag SNPs). Zero HLA-B and ERAP1 risk alleles were defined as the reference risk genotype (i.e., OR=1), and assessed the risk of the ERAP1 risk allele on a B27 negative background (left panel, FIG. 3), compared to having one HLA-B27 allele (middle panel) and two copies of HLA-B27 or subjects carrying the HLA-B27 and HLA-B40 risk alleles (right panel). A moderate risk increase of OR=4.5 when carrying one HLA-B27 allele, which almost doubled with ERAP1 risk genotypes to OR=7.5, was observed. The maximum risk was with two HLA risk alleles and the full ERAP1 risk genotype, which nearly tripled the risk to OR=12.5. Taken together, these results suggest that a decreased expression of ERAP1 will decrease the risk for AU, and this effect is strongest in a HLA-B risk background.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

SEQUENCE LISTING

The patent contains a lengthy sequence listing. A copy of the sequence listing is available in electronic form from the USPTO web site (https://seqdata.uspto.gov/?pageRequest=docDetail&DocID=US12157891B2). An electronic copy of the sequence listing will also be available from the USPTO upon request and payment of the fee set forth in 37 CFR 1.19(b)(3).

What is claimed is:

1. A method of treating a human subject with a therapeutic agent that treats or inhibits uveitis, wherein the human subject has uveitis, the method comprising the steps of:
   determining whether the human subject has an Endoplasmic Reticulum Aminopeptidase 1 (ERAP1) variant nucleic acid molecule encoding Lys528Arg or Asp575Asn by:
      obtaining or having obtained a biological sample from the human subject;
      performing or having performed a sequence analysis on the biological sample to determine if the human subject has a genotype comprising the ERAP1 variant nucleic acid molecule; and
      detecting the presence or absence of HLA-B27 in the biological sample; and
   administering or continuing to administer to the human subject the therapeutic agent that treats or inhibits uveitis in a standard dosage amount to a human subject that is ERAP1 reference and is HLA-B27 positive, and/or administering to the human subject an antisense nucleic acid molecule or a small interfering RNA (siRNA) that hybridizes to an Endoplasmic Reticulum Aminopeptidase 1 (ERAP1) nucleic acid molecule; or
   administering or continuing to administer to the human subject the therapeutic agent that treats or inhibits uveitis in an amount that is the same as or less than a standard dosage amount to a human subject that is heterozygous for the ERAP1 variant nucleic acid molecule and is HLA-B27 positive, and/or administering to the human subject an antisense nucleic acid molecule or a small interfering RNA (siRNA) that hybridizes to an Endoplasmic Reticulum Aminopeptidase 1 (ERAP1) nucleic acid molecule;
   wherein the presence of a genotype having the ERAP1 variant nucleic acid molecule encoding Lys528Arg or Asp575Asn indicates the human subject has a decreased risk of developing uveitis.

2. The method according to claim 1, wherein the uveitis comprises anterior uveitis, acute anterior uveitis, or pan-uveitis.

3. The method according to claim 2, wherein the acute anterior uveitis comprises iridocyclitis or iritis.

4. The method according to claim 1, wherein the ERAP1 variant nucleic acid molecule is:
   a genomic nucleic acid molecule having a nucleotide sequence comprising: a guanine at a position corresponding to position 19,474 according to SEQ ID NO:2, an adenine at a position corresponding to position 21,595 according to SEQ ID NO:3, a cytosine at a position corresponding to position 21,811 according to SEQ ID NO:4, or a thymine at a position corresponding to position 42,579 according to SEQ ID NO:5;
   an mRNA molecule having a nucleotide sequence comprising: a guanine at a position corresponding to position 1,841 according to SEQ ID NO:7, or an adenine at a position corresponding to position 1,981 according to SEQ ID NO:8; or
   a cDNA molecule produced from an mRNA molecule, wherein the cDNA molecule has a nucleotide sequence comprising: a guanine at a position corresponding to position 1,841 according to SEQ ID NO:10, or an adenine at a position corresponding to position 1,981 according to SEQ ID NO:11.

5. The method according to claim 1, wherein the antisense nucleic acid molecule comprises a nucleotide sequence selected from the group consisting of SEQ ID NOs: 35-784, and wherein the siRNA molecule comprises a sense strand and a corresponding antisense strand selected from the group consisting of SEQ ID NOs: 785-2578.

6. The method according to claim 1, the method further comprising administering to the subject an HLA-B27 inhibitor selected from an HLA-B27 antibody, an HLA-B27 antisense nucleic acid molecule, or an HLA-B27 siRNA molecule.

7. The method according to claim 6, wherein the HLA-B27 inhibitor comprises an HLA-B27 antibody.

8. The method according to claim 6, wherein the HLA-B27 antisense nucleic acid molecule comprises a nucleotide sequence selected from the group consisting of SEQ ID NOS: 2579-2923.

9. The method according to claim 6, wherein the HLA-B27 siRNA molecule comprises a sense strand and a corresponding antisense strand selected from the group consisting of SEQ ID NOs: 2924-3661.

\* \* \* \* \*